United States Patent
Coates et al.

(10) Patent No.: US 10,080,758 B2
(45) Date of Patent: Sep. 25, 2018

(54) TOSYLATE SALT OF N-[3-[(4AR,7AS)-2-AMINO-6-(5-FLUOROPYRIMIDIN-2-YL)-4,4A,5,7-TETRAHYDROPYRROLO[3,4-D][1,3]THIAZIN-7A-YL]-4-FLUORO-PHENYL]-5-METHOXY-PYRAZINE-2-CARBOXAMIDE

(71) Applicant: Eli Lilly and Company, Indianapolis, IN (US)

(72) Inventors: David Andrew Coates, Indianapolis, IN (US); Craig Daniel Wolfangel, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/535,523

(22) PCT Filed: Jan. 22, 2016

(86) PCT No.: PCT/US2016/014423
§ 371 (c)(1),
(2) Date: Jun. 13, 2017

(87) PCT Pub. No.: WO2016/122968
PCT Pub. Date: Aug. 4, 2016

(65) Prior Publication Data
US 2017/0368071 A1    Dec. 28, 2017

Related U.S. Application Data

(60) Provisional application No. 62/109,733, filed on Jan. 30, 2015.

(51) Int. Cl.
*C07D 513/04*  (2006.01)
*A61K 31/542*  (2006.01)

(52) U.S. Cl.
CPC .......... *A61K 31/542* (2013.01); *C07D 513/04* (2013.01)

(58) Field of Classification Search
CPC .................................................. C07D 513/04
USPC ........................................ 544/48; 514/224.2
See application file for complete search history.

(56) References Cited

U.S. PATENT DOCUMENTS 8,841,293 B1 *  9/2014  Green ................. A61K 31/542
                                                     514/224.2
8,987,254 B2     3/2015  Green et al.
9,828,390 B2 *  11/2017  Coates et al. ........ C07D 513/04
                                                     514/224.2

FOREIGN PATENT DOCUMENTS

WO        2014/143579 A1      9/2014

OTHER PUBLICATIONS

Berge, S.M., et al.,"Pharmaceutical Salts", Journal of Pharmaceutical Sciences, vol. 66, pp. 1-19 (1977).
International Search Report of the International Searching Authority for PCT/US2016/014423.
Pending U.S. Appl. No. 15/504,398, filed Feb. 16, 2017, Eli Lilly and Company.
Written Opinion of the International Searching Authority for PCT/US2016/014423.
Berge, S.M., D. Bighley and D.C. Monkhouse, "Pharmaceutical Salts," J. Pharm. Sci., vol. 66, No. 1, pp. 1-16, 1977.
Elder, Delaney, Teasdale et al., "The Utility of Sulfonate Salts in Drug Development," J. Pharm. Sci., vol. 99, No. 7, pp. 2948-2961, Jul. 2010.

* cited by examiner

*Primary Examiner* — Kahsay Habte
(74) *Attorney, Agent, or Firm* — Nelson L. Lentz

(57) ABSTRACT

The present invention provides a tosylate salt of N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide.

5 Claims, No Drawings

TOSYLATE SALT OF N-[3-[(4AR,7AS)-2-AMINO-6-(5-FLUOROPYRIMIDIN-2-YL)-4,4A,5,7-TETRAHYDROPYRROLO[3,4-D][1,3]THIAZIN-7A-YL]-4-FLUORO-PHENYL]-5-METHOXY-PYRAZINE-2-CARBOXAMIDE

The present invention relates to a toluenesulfonic acid (tosylate) salt of N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide, to pharmaceutical compositions comprising the tosylate salt, to methods of using the tosylate salt to treat physiological disorders, and to intermediates and processes useful in the synthesis thereof.

The present invention is in the field of treatment of Alzheimer's disease and other diseases and disorders involving amyloid β (Abeta) peptide, a neurotoxic and highly aggregatory peptide segment of the amyloid precursor protein (APP). Alzheimer's disease is a devastating neurodegenerative disorder that affects millions of patients worldwide. In view of the currently approved agents on the market which afford only transient, symptomatic benefits to the patient, there is a significant unmet need in the treatment of Alzheimer's disease.

Alzheimer's disease is characterized by the generation, aggregation, and deposition of Abeta in the brain. Complete or partial inhibition of β-secretase (β-site amyloid precursor protein-cleaving enzyme; BACE) has been shown to have a significant effect on plaque-related and plaque-dependent pathologies in mouse models suggesting that even small reductions in Abeta peptide levels might result in a long-term significant reduction in plaque burden and synaptic deficits, thus providing significant therapeutic benefits, particularly in the treatment of Alzheimer's disease.

U.S. Pat. No. 8,841,293 discloses certain BACE inhibitors for treatment of Abeta peptide-mediated disorders, such as Alzheimer's disease, and in particular, discloses for example the BACE inhibitor N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide and the corresponding hydrochloride salt.

Novel forms of N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide are desired which provide for improved solid state stability and chemical stability for enhanced utilization in the preparation and manufacture of pharmaceutical formulations. Accordingly, the present invention provides a tosylate salt of N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide. In addition, the present invention provides the tosylate salt of N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide which is crystalline. The present invention further provides the tosylate salt of N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide which is characterized by a substantial peak in the X-ray diffraction spectrum, at diffraction angle 2-theta of 5.0° in combination with one or more of the peaks selected from the group consisting of 19.6°, 13.8°, and 18.5°; with a tolerance for the diffraction angles of 0.2 degrees.

The present invention also provides a method of treating Alzheimer's disease in a patient, comprising administering to a patient in need of such treatment an effective amount of a tosylate salt of N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide. The present invention further provides a method of treating the progression of mild cognitive impairment to Alzheimer's disease in a patient, comprising administering to a patient in need of such treatment an effective amount of a tosylate salt of N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide. The present invention also provides a method of inhibiting BACE in a patient, comprising administering to a patient in need of such treatment an effective amount of a tosylate salt of N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide.

The present invention also provides a method for inhibiting BACE-mediated cleavage of amyloid precursor protein, comprising administering to a patient in need of such treatment an effective amount of a tosylate salt of N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide. The invention further provides a method for inhibiting production of Abeta peptide, comprising administering to a patient in need of such treatment an effective amount of a tosylate salt of N-[3-[(4aR,7aS)-2-amino-6-(5-fluoropyrimidin-2-yl)-4,4a, 5,7-tetrahydropyrrolo[3,4-d][1,3]thiazin-7a-yl]-4-fluoro-phenyl]-5-methoxy-pyrazine-2-carboxamide.

Furthermore, this invention provides a tosylate salt of N-[3-[(4aR,7aS)-2-amino-6-(5-fluoropyrimidin-2-yl)-4,4a, 5,7-tetrahydropyrrolo[3,4-d][1,3]thiazin-7a-yl]-4-fluoro-phenyl]-5-methoxy-pyrazine-2-carboxamide for use in therapy, in particular for the treatment of Alzheimer's disease or for the treatment of the progression of mild cognitive impairment to Alzheimer's disease. Even furthermore, this invention provides the use of a tosylate salt of N-[3-[(4aR, 7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide for the manufacture of a medicament for the treatment of Alzheimer's disease or for the treatment of the progression of mild cognitive impairment to Alzheimer's disease.

In addition, the invention provides a method of treating Alzheimer's disease in a patient, comprising administering to a patient in need of such treatment an effective amount of a tosylate salt of N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide which is characterized by a substantial peak in the X-ray diffraction spectrum, at diffraction angle 2-theta of 5.0° in combination with one or more of the peaks selected from the group consisting of 19.6°, 13.8°, and 18.5°; with a tolerance for the diffraction angles of 0.2 degrees. The invention also provides a tosylate salt of N-[3-[(4aR,7aS)-2-amino-6-(5-fluoropyrimidin-2-yl)-4,4a,5,7-tetrahydropyrrolo[3,4-d][1, 3]thiazin-7a-yl]-4-fluoro-phenyl]-5-methoxy-pyrazine-2-carboxamide which is characterized by a substantial peak in the X-ray diffraction spectrum, at diffraction angle 2-theta of 5.0° in combination with one or more of the peaks selected from the group consisting of 19.6°, 13.8°, and 18.5°; with a tolerance for the diffraction angles of 0.2 degrees for use in therapy, in particular for the treatment of Alzheimer's disease or for the treatment of the progression of mild cognitive impairment to Alzheimer's disease. Furthermore, the invention provides a tosylate salt of N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide which is characterized by a substantial peak in the X-ray diffraction spectrum, at diffraction angle 2-theta of 5.0° in combination with one or more of the peaks selected from the group consisting of 19.6°, 13.8°, and 18.5°; with a tolerance for the diffraction angles of 0.2 degrees, for the manufacture of a medicament for the treatment of Alzheimer's disease or for the treatment of the progression of mild cognitive impairment to Alzheimer's disease.

The invention further provides a pharmaceutical composition, comprising the tosylate salt of N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide with one or more pharmaceutically acceptable carriers, diluents, or excipients. This invention also encompasses novel intermediates and processes for the synthesis of the tosylate salt of N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide.

Mild cognitive impairment has been defined as a potential prodromal phase of dementia associated with Alzheimer's disease based on clinical presentation and on progression of patients exhibiting mild cognitive impairment to Alzheimer's dementia over time. (Morris, et al., *Arch. Neurol.*, 58, 397-405 (2001); Petersen, et al., *Arch. Neurol.*, 56, 303-308 (1999)). The term "treatment of the progression of mild cognitive impairment to Alzheimer's disease" includes slowing, arresting, or reversing the progression of mild cognitive impairment to Alzheimer's disease in a patient.

As used herein, the terms "treating" or "to treat" includes restraining, slowing, stopping, or reversing the progression or severity of an existing symptom or disorder.

As used herein, the term "patient" refers to a human.

The term "inhibition of production of Abeta peptide" is taken to mean decreasing of in vivo levels of Abeta peptide in a patient.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be readily determined by the attending diagnostician, as one skilled in the art, by the use of known techniques and by observing results obtained under analogous circumstances. In determining the effective amount for a patient, a number of factors are considered by the attending diagnostician, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds of the present invention are generally effective over a wide dosage range. For example, dosages per day normally fall within the range of about 0.01 to about 20 mg/kg of body weight. In some instances dosage levels below the lower limit of the aforesaid range may be more than adequate, while in other cases still larger doses may be employed with acceptable side effects, and therefore the above dosage range is not intended to limit the scope of the invention in any way.

The compounds of the present invention are preferably formulated as pharmaceutical compositions administered by any route which makes the compound bioavailable, including oral, transdermal, and parenteral routes. Most preferably, such compositions are for oral administration or transdermal, with oral administration being especially preferred. Such pharmaceutical compositions and processes for preparing same are well known in the art. (See, e.g., Remington: The Science and Practice of Pharmacy (D. B. Troy, Editor, 21st Edition, Lippincott, Williams & Wilkins, 2006).

The tosylate salt of N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide is particularly useful in the treatment methods of the invention, but certain forms are preferred. The following paragraphs describe such forms. It will be understood that these preferences are applicable to the pharmaceutical compositions, the treatment methods, and to the new compounds of the invention.

Crystalline tosylate salt of N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide which is characterized by a substantial peak in the X-ray diffraction spectrum, at diffraction angle 2-theta of 5.0° in combination with one or more of the peaks selected from the group consisting of 19.6°, 13.8°, and 18.5°; with a tolerance for the diffraction angles of 0.2 degrees is particularly preferred.

One of ordinary skill in the art will appreciate that N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide can exist in tautomeric forms, as depicted in Scheme A. When any reference in this application to one of the specific tautomers of N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide is given, it is understood to encompass both tautomeric forms and all mixtures thereof.

Scheme A

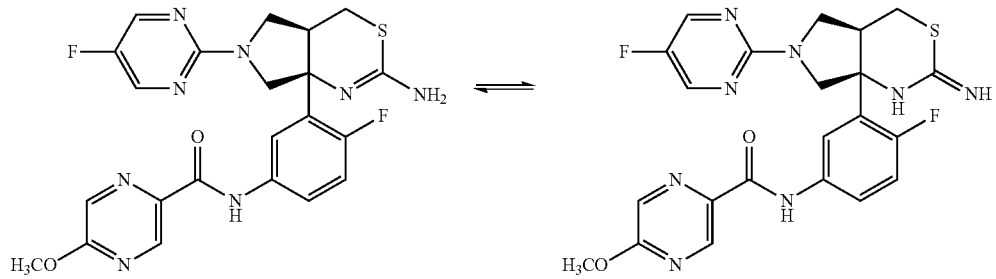

Additionally, certain intermediates described in the following schemes may contain one or more nitrogen protecting groups. The variable protecting group may be the same or different in each occurrence depending on the particular reaction conditions and the particular transformations to be performed. The protection and deprotection conditions are well known to the skilled artisan and are described in the literature (See for example "*Greene's Protective Groups in Organic Synthesis*", Fourth Edition, by Peter G. M. Wuts and Theodora W. Greene, John Wiley and Sons, Inc. 2007).

Certain stereochemical centers have been left unspecified and certain substituents have been eliminated in the following schemes for the sake of clarity and are not intended to limit the teaching of the schemes in any way. Furthermore, individual isomers, enantiomers, and diastereomers may be separated or resolved by one of ordinary skill in the art at any convenient point in the synthesis of compounds of the invention, by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994). The designations "isomer 1" and "isomer 2" refer to the compounds that elute from chiral chromatography first and second, respectively, and if chiral chromatography is initiated early in the synthesis, the same designation is applied to subsequent intermediates and examples.

Certain abbreviations are defined as follows: "acetonitrile" refers to ACN; "APP" refers to amyloid precursor protein; "CSF" refers to cerebrospinal fluid; "DCM" refers to dichloromethane; "DIPEA" refers to diisopropylethylamine, N-ethyl-N-isopropyl-propan-2-amine, or N,N-diisopropylethylamine; "DMEM" refers to Dulbecco's Modified Eagle's Medium; "DMF" refers to dimethylformamide; "DMSO" refers to dimethyl sulfoxide; "EDCI" refers to 1-(3-dimethylaminopropyl)-3-ethylcarbodiimide hydrochloride; "ee" refers to enantiomeric excess; "EtOAc" refers to ethyl acetate; "Ex" refers to example; "F12" refers to Ham's F12 medium; "FBS" refers to Fetal Bovine Serum; "FRET" refers to fluorescence resonance energy transfer; "HEK" refers to human embryonic kidney; "HOAc" refers to acetic acid; "HOBt" refers to 1-hydroxylbenzotriazole hydrate; "HPLC" refers to high-performance liquid chromatography; "IC$_{50}$" refers to the concentration of an agent that produces 50% of the maximal inhibitory response possible for that agent; "min" refers to minute or minutes; "MTBE" refers to methyl tert-butyl ether; "PDAPP" refers to platelet derived amyloid precursor protein; "Prep" refers to preparation; "RFU" refers to relative fluorescence unit; "SCX" refers to strong cation exchange; "R$_t$" refers to retention time; and "THF" refers to tetrahydrofuran.

It is understood by one of ordinary skill in the art that the terms "tosylate", "toluenesulfonic acid", "p-toluenesulfonic acid", and "4-methylbenzene sulfonic acid" refer to the compound of the following structure:

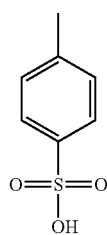

As such, it is understood by one of ordinary skill in the art that a reference herein to any of the following names:

"the tosylate salt of N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide";

"N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide; toluenesulfonic acid";

"N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide; p-toluenesulfonic acid"; and "N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide; 4-methylbenzene sulfonic acid"; refers to the salt of the following structure:

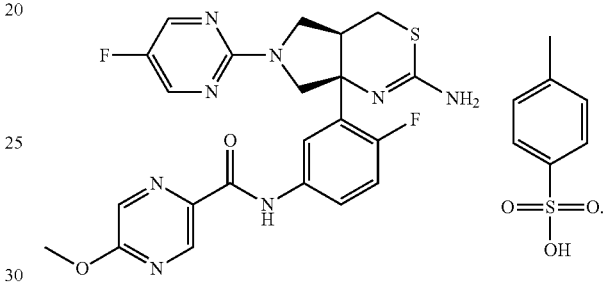

The tosylate salt of N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide may be prepared by a variety of procedures known in the art, some of which are illustrated in the Preparations and Examples below. In addition, N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide free base and the corresponding HCl salt may be prepared by one of ordinary skill in the art as described in U.S. Pat. No. 8,841,293. The specific synthetic steps for each of the routes described may be combined in different ways, or in conjunction with steps from different preparations to prepare compounds of the invention. The products of each step can be recovered by conventional methods well known in the art, including extraction, evaporation, precipitation, chromatography, filtration, trituration, or crystallization. The reagents and starting materials are readily available to one of ordinary skill in the art.

PREPARATION 1

2-Bromo-1-(5-bromo-2-fluoro-phenyl)ethanone

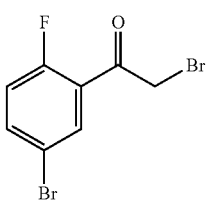 [SMILES: O=C(CBr)c1cc(Br)ccc1F]

N-bromosuccinimide (984 g, 5.53 mol) is added portionwise to a solution of 1-(5-bromo-2-fluoro-phenyl)ethanone (1000 g, 4.6 mol) and p-toluenesulfonic acid (1315 g, 7.64 mol) in DCM (7 L) at 35° C. The mixture is stirred and heated to 40° C. for 4 hours. The mixture is cooled to 24° C., and 7% NaHCO₃ (5 L) is added. The layers are separated and the organic layer is washed with 10% Na₂SO₃ (5 L) and water (5 L). The organic layer is concentrated to 2-3 volumes to give the title compound which is used without further purification.

ALTERNATE PREPARATION 1

1-(5-Bromo-2-fluoro-phenyl)ethanone (80 g, 0.37 mol) is dissolved in DCM (800 mL) and cooled to 10° C. Bromine (63 g, 0.39 mol) is added slowly over 5 hours. After 30 minutes, additional bromine (3.5 g, 0.06 mol) is added. After 30 minutes, the mixture is warmed to room temperature and the organic layer is washed with a mixture of aqueous NaCl (500 mL) and aqueous NaHCO₃ (400 mL). The organic layer is washed successively with aqueous NaHCO₃ (400 mL), aqueous NaHSO₃ (2×400 mL), and aqueous NaCl. The organic layer is dried (Na₂SO₄) and concentrated to a residue. The residue is dissolved in a mixture of DCM (100 mL) and petroleum ether (500 mL). The solution is cooled to −50° C. for 0.5 hour and the solid is collected by filtration to give the title compound (84 g, 77%). ¹H NMR (CDCl₃) δ 4.46 (d, 2H), 7.07 (dd, 1H), 7.66 (m, 1H), 8.02 (dd, 1H).

PREPARATION 2

2-[Allyl(benzyl)amino]-1-(5-bromo-2-fluoro-phenyl) ethanone

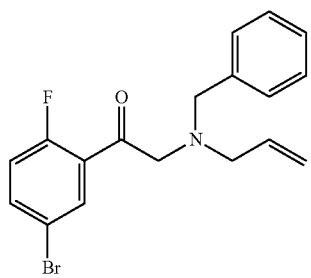 [SMILES: C=CCN(CC(=O)c1cc(Br)ccc1F)Cc1ccccc1]

2-Bromo-1-(5-bromo-2-fluoro-phenyl)ethanone (25.1 g, 84.8 mmol) is added to a solution of N-benzylprop-2-en-1-amine (15.0 g, 102 mmol) in toluene (200 mL) and DIPEA (59 mL, 338 mmol) at room temperature. The mixture is deoxygenated by stirring at room temperature for 10 minutes while subsurface sparging nitrogen through the mixture. The reaction is heated to 40° C., stirred for 2.5 hours, and then additional N-benzylpro-2-en-1-amine (2.0 g, 13.6 mmol) is added. The reaction is stirred at 40° C. for 4.5 hours and then cooled to room temperature. The material is used without further purification. The solution is analyzed by HPLC for the title compound using the following parameters: LC column: Waters Acquity Ultra Performance Liquid Chromatography (UPLC®) C 8 2.1×100 mm 1.7 µm; mobile phase A: 0.1% (vol/vol) TFA in water+0.2% ACN (vol/vol), prepared by adding TFA (4 mL) and ACN (10 mL) to water (4 L), mobile phase B: 0.1% TFA in ACN, prepared by adding TFA (4 mL) to ACN (4 L). Gradient: % A=95% to 53.1% over 10 minutes, flow rate 0.85 mL/minutes, column temperature: 45° C. R$_t$=6.43 minutes (UV)

PREPARATION 3

5-Allyl-6a-(5-bromo-2-fluoro-phenyl)-1-[(4-methoxyphenyl)methyl-3,3a,4,6-tetrahydropyrrolo[3,4-c]isoxazole

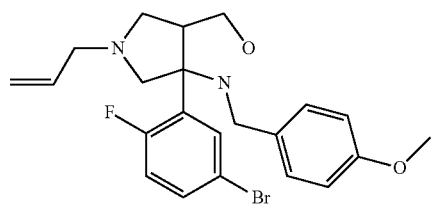 [SMILES: C=CCN1CC(CO)C(NCc2ccc(OC)cc2)(c2cc(Br)ccc2F)C1]

To a solution of 2-bromo-1-(5-bromo-2-fluoro-phenyl) ethanone (1363 g, 4.61 mol) in toluene (10 L) is added diallylamine (537 g, 5.53 mol) and DIPEA (2381 g, 18.42 mol). The mixture is stirred for 4 hours at 40° C. to give 1-(5-bromo-2-fluoro-phenyl)-2-(diallylamino)ethanone, which is not isolated. N-(4-methoxybenzyl)hydroxylamine (847 g, 5.53 mol) and titanium (IV) isopropoxide (1965 g, 6.91 mol) are added to the mixture containing crude 1-(5-bromo-2-fluoro-phenyl)-2-(diallylamino)ethanone. The mixture is stirred at 90° C. for 2 hours. The mixture is cooled to 20° C., and 50% citric acid monohydrate (4 L) and saturated Na₂CO₃ (4 L) are added. The layers are separated and the aqueous is extracted with MTBE (5 L). The organic extract is washed with water (5 L), and filtered through diatomaceous earth and concentrated to dryness. EtOAc (10 L) and oxalic acid (580 g) are added to the residue and a solid is filtered and added to 1 N NaOH (13 L). MTBE (5 L) is added and the mixture is filtered through diatomaceous earth. The layers are separated and the organic layer is concentrated to 2 volumes. Heptane (3 L) is added and the solution is cooled to 10° C. The resulting solid is filtered to give the title compound (1330 g, 64%). ¹H NMR (400 MHz, CDCl₃) δ 2.51-2.49(m, 3H), 3.09-3.04(m, 3H), 3.78-3.41(m, 6H), 4.01(m, 1H), 5.24-5.01(m, 2H), 5.89-5.85(m, 1H), 6.82-6.80(m, 2H), 7.51-7.13(m, 3H), 7.63-7.62(m, 1H), 7.65-7.64(m, 1H).

PREPARATION 4

Relative-(3aR,6aS)-5-Benzyl-6a-(5-bromo-2-fluoro-phenyl)-1-[(4-methoxyphenyl)methyl]-3,3a,4,6-tetrahydropyrrolo[3,4-c]isoxazole, oxalic acid

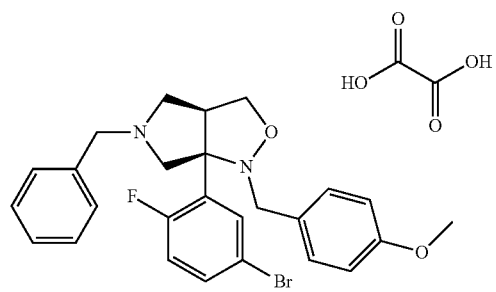 [SMILES: COc1ccc(CN2OC[C@@H]3CN(Cc4ccccc4)C[C@@]32c2cc(Br)ccc2F)cc1 ; O=C(O)C(=O)O]

N-[(4-Methoxyphenyl)methyl]hydroxylamine (15.5 g, 101 mmol) is added to the solution of 2-[allyl(benzyl)amino]-1-(5-bromo-2-fluoro-phenyl)ethanone at 40° C., followed by titanium (IV) isopropoxide (50.3 mL, 169 mmol). The mixture is deoxygenated by sparging nitrogen through the system for 5 minutes. The mixture is heated to 90° C. with stirring for 2 hours. The reaction mixture is washed with a solution of citric acid (36 g, 186 mmol) in water (36 g) and stirred for 30 minutes at room temperature. Sodium carbonate (100 g, 939 mmol) is added as a saturated solution in water and the pH is adjusted to approximately 9. The mixture is diluted with water and toluene as needed to separate the layers. The toluene layer is washed with a solution of HCl in water (5.1 mL of 5 N HCl) diluted with water (200 mL) followed by water (200 mL). The toluene layer is concentrated to a thick oil. The oil is dissolved in EtOAc (375 mL) and a solution of oxalic acid (15.4 g, 169 mmol) dissolved in EtOAc (375 mL) is added dropwise with stirring at room temperature. The mixture is stirred at room temperature for 2 days, filtered, and the product cake is washed with EtOAc (250 mL). The solid is dried overnight in vacuo at 40° C. to give the title compound as a cis racemic mixture (41.7 g, 84%). ES/MS (m/z): 498 (M+H).

PREPARATION 5

Relative N-[3-[(3aR,6aS)-5-Benzyl-1-[(4-methoxyphenyl)methyl]-3,3a,4,6-tetrahydropyrrolo[3,4-c]isoxazol-6a-yl]-4-fluoro-phenyl]-2,2,2-trifluoro-acetamide

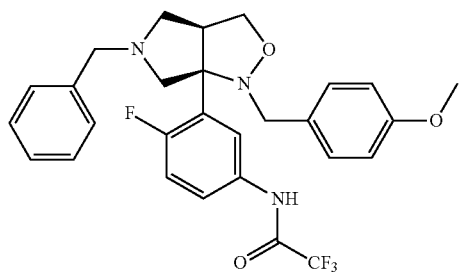 [SMILES: COc1ccc(CN2OC[C@@H]3CN(Cc4ccccc4)C[C@@]32c2cc(NC(=O)C(F)(F)F)ccc2F)cc1]

Relative-(3aR,6aS)-5-benzyl-6a-(5-bromo-2-fluoro-phenyl)-1-[(4-methoxyphenyl)methyl]-3,3a,4,6-tetrahydropyrrolo[3,4-c]isoxazole, oxalic acid (23.6 g, 40.2 mmol) is added to a mixture of DCM (400 mL) and 5 N NaOH aqueous solution (200 mL). The mixture is stirred for 10 minutes and then the layers are separated. The organic layer is concentrated to give relative-(3aR,6aS)-5-benzyl-6a-(5-bromo-2-fluoro-phenyl)-1-[(4-methoxyphenyl)methyl]-3,3a,4,6-tetrahydropyrrolo[3,4-c]isoxazole (20.0 g, 40.2 mmol). This material is added to dimethyl sulfoxide (360 mL), 2,2,2-trifluoroacetamide (7.8 g, 68 mmol), sodium iodide (10.3 g, 68.6 mmol), potassium carbonate (9.54 g, 68.3 mmol), (1R,2R)—N,N'-dimethyl-1,2-cyclohexanediamine (4.7 g, 32 mmol), and copper (I) iodide (1.53 g, 8.03 mmol). The mixture is deoxygenated by sparging nitrogen through the system for 10 minutes. The mixture is heated to 115° C., stirred for 5.5 hours, and cooled to room temperature. EtOAc (250 mL) and water (200 mL) are added and the resultant mixture is stirred for 10-15 minutes. The layers are separated and the aqueous layer is back extracted with EtOAc (200 mL). The combined organic layers are washed with ammonium chloride solution 20 wt % aqueous (100 mL) followed by lithium chloride solution 20 wt % aqueous (100 mL) and water (100 mL). The organic layer is dried over magnesium sulfate, filtered, and concentrated to dryness to give the crude title compound as a racemic cis mixture (23.6 g, 111%). ES/MS (m/z): 530 (M+H).

PREPARATION 6

Relative-3-[(3aR,6aS)-5-Benzyl-1-(4-methoxyphenyl)methyl]-3,3a,4,6-tetrahydropyrrolo[3,4-c]isoxazol-6a-yl]-4-fluoro-aniline

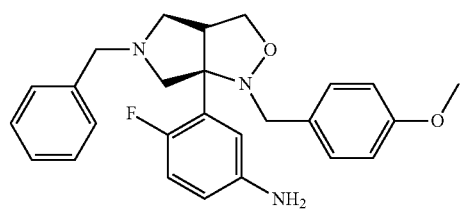

Relative N-[3-[(3aR,6aS)-5-benzyl-1-[(4-methoxyphenyl)methyl]-3,3a,4,6-tetrahydropyrrolo[3,4-c]isoxazol-6a-yl]-4-fluoro-phenyl]-2,2,2-trifluoro-acetamide (21.0 g, 39.7 mmol) is added to methanol (250 mL), 5 N aqueous NaOH (105 mL), and ethanol (105 mL) and the resultant mixture is heated to 50° C. for 2 hours. The reaction mixture is concentrated under reduced pressure at 35-40° C. to remove methanol and ethanol. The material is dissolved in a mixture of MTBE (320 mL) and water (300 mL). The layers are separated and the organic layer is washed with water (100 mL) followed by a mixture of water (400 mL) and 12 N aqueous HCl (3.5 mL). The aqueous layer is added to a mixture of MTBE (400 mL), water (100 mL), and 5 N aqueous NaOH (25 mL) and the layers are separated. The aqueous layer is washed with MTBE (100 mL). The organic layers are combined, dried over magnesium sulfate, filtered, and concentrated in vacuo to give the title compound as a racemic cis mixture (9.8 g, 57%). ES/MS (m/z): 435 (M+H).

PREPARATION 7

Relative-N-3-[(3aR,6aS)-5-Benzyl-1-[(4-methoxyphenyl)methyl]-3,3a,4,6-tetrahydropyrrolo[3,4-c]isoxazol-6a-yl]-4-fluoro-phenyl]acetamide

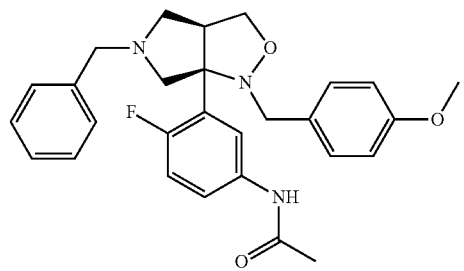 [SMILES: COc1ccc(CN2OC[C@@H]3CN(Cc4ccccc4)C[C@@]32c2cc(NC(C)=O)ccc2F)cc1]

Relative-3-[(3aR,6aS)-5-benzyl-1-(4-methoxyphenyl)methyl]-3,3a,4,6-tetrahydropyrrolo[3,4-c]isoxazol-6a-yl]-4-fluoro-aniline (9.4 g, 22 mmol) is added to DCM (110 mL), 4-dimethylaminopyridine (0.08 g, 0.65 mmol), and triethylamine (6.1 mL, 43 mmol) and the reaction is cooled to 0°

C. Acetic anhydride (3.4 g, 33 mmol) is added to the solution dropwise. The reaction is warmed to room temperature and stirred for 2 hours. Water (140 mL) is added to the reaction and the mixture is stirred at room temperature for 10 minutes. The layers are separated and the aqueous layer is washed with DCM (100 mL). The combined organic layers are dried over magnesium sulfate, filtered, and concentrated to give the title compound as a racemic cis mixture (10.1 g, 100%). ES/MS (m/z): 477 (M+H).

PREPARATION 8

5-Allyl-6a-(5-bromo-2-fluoro-phenyl)-3,3a,4,6-tetra-hydro-1H-pyrrolo[3,4-c]isoxazole hydrochloride

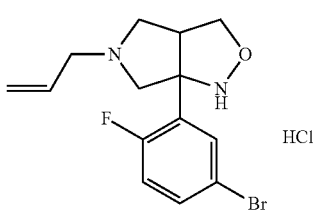 [SMILES: C=CCN1CC2CONC2(c2cc(Br)ccc2F)C1 ; Cl]

TFA (4 L, 52.9 mol) is added dropwise to a solution of 5-allyl-6a-(5-bromo-2-fluoro-phenyl)-1-[(4-methoxyphenyl)methyl-3,3a,4,6-tetrahydropyrrolo[3,4-c]isoxazole (1990 g, 4.45 mol) in DCM (12 L) at a rate to maintain the temperature below 35° C. After the addition is complete, the mixture is warmed to 33-43° C. and stirred for 6 hours.

NaOH (20%, 10 L) is added at a rate to maintain the temperature below 35° C. The layers are separated and the organic layer is washed with water (6 L). The solution is concentrated, ethanol (16 L) is added, and the mixture is filtered through diatomaceous earth. The filtrate is concentrated and EtOAc (10 L) is added. 4 M HCl in EtOAc (8 L) is added and the resulting solid is filtered and dried to give the title compound (1385 g, 85.6%). ES/MS (m/z): 327.1 (M+H)

PREPARATION 9

[1-Allyl-4-amino-4-(5-bromo-2-fluoro-phenyl)pyrrolidin-3-yl]methanol

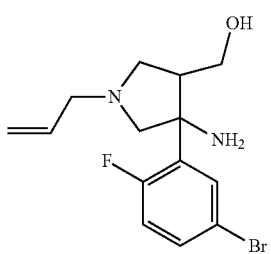 [SMILES: C=CCN1CC(CO)C(N)(c2cc(Br)ccc2F)C1]

A saturated aqueous solution of sodium carbonate is added to a solution of 5-allyl-6a-(5-bromo-2-fluoro-phenyl)-3,3a,4,6-tetrahydro-1H-pyrrolo[3,4-c]isoxazole hydrochloride (1400 g, 3.85 mol) in DCM (7 L) to reach a pH>9. The layers are separated and the organic extract concentrated to 1.5 volumes. HOAc (1.38 L) is added and the solution concentrated to 2 L. HOAc (7 L) and zinc powder (2.5 kg, 38.5 mol) are added and the mixture is heated to 40-50° C. and stirred for 3 hours. EtOAc (9.8 L) is added and the mixture is filtered through diatomaceous earth. The filter cake is washed with EtOAc (4 L). The filtrate is separated and water (7 L) is added to the combined organics Ammonium hydroxide is added to reach a pH The layers are separated and the organic layer is concentrated to 2 L. Ethanol (2.8 L) is added and the solution is concentrated to 2 L. Ethanol (19 L) is added and the mixture is filtered through diatomaceous earth to give an ethanol solution of the title compound, which is used without further purification.

PREPARATION 10

[(3S,4R)-1-allyl-3-(5-bromo-2-fluoro-phenyl)-4-(hydroxymethyl)pyrrolidin-3-yl]ammonium; (2S,3S)-4-hydroxy-2,3-bis[(4-methylbenzoyl)oxy]-4-oxo-butanoate

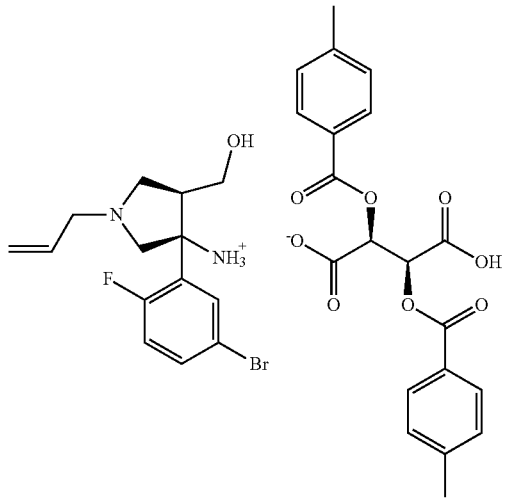

Di-p-toluoyl-L-tartaric acid monohydrate (1.04 kg, 2.69 mol) is added to a solution of [1-allyl-4-amino-4-(5-bromo-2-fluoro-phenyl)pyrrolidin-3-yl]methanol (1264 g. 3.85 mmol) in ethanol (21 L). The mixture is heated to 65-75° C. and stirred for 3 hours. The mixture is cooled to 5-10° C., a seed crystal is added of [(3S,4R)-1-allyl-3-(5-bromo-2-fluoro-phenyl)-4-(hydroxymethyl)pyrrolidin-3-yl]ammonium; (2S,3 S)-4-hydroxy-2,3-bis[(4-methylbenzoyl)oxy]-4-oxo-butanoate (1.0 g), and the mixture is stirred for 3 hours. The solid is filtered and the filter cake is washed with cold ethanol (1.4 L). The filter cake is dried to give the title compound as a white solid. Chiral analysis of the second eluting isomer: Column: IC Chiralpak, 4.6 mm*250 mm*5 µm; eluent: 90% hexane (0.3% diethylamine): 10% ethanol (0.3% diethylamine); flow rate of 1.0 mL/min at UV 270 nm confirms the enantiomerically enriched (99% ee) enantiomer with $R_t$=7.4 minutes, (1050 g, 38%). $^1$H NMR (400 MHz, CD$_3$OD) δ 2.40 (s, 6H), 3.05-3.04(m, 1H), 3.57-3.31(m, 3H), 3.66-3.58(m, 4H), 3.75-3.74(m, 2H), 5.38-5.36(m, 1H), 5.50-5.46(m, 1H), 5.88 (s, 2H), 5.97-5.91(m, 1H), 7.10-7.05 (m, 1H), 7.29 (d, J=8.0 Hz, 4H), 7.53-7.51(m, 1H), 7.80-7.78(m, 1H), 8.01 (d, J=8.0 Hz, 4H).

PREPARATION 11

Relative-1-[3-[(3S,4R)-3-Amino-4-(hydroxymethyl)pyrrolidin-3-yl]-4-fluoro-phenyl]propan-2-one, di-toluenesulfonic acid

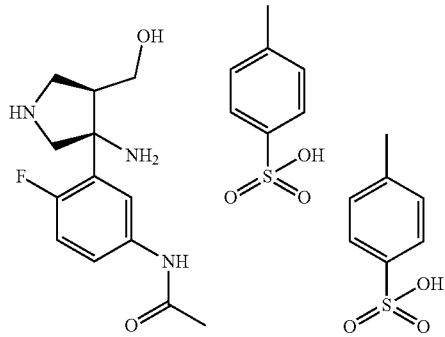

Relative-N-3-[(3aR,6aS)-5-benzyl-1-[(4-methoxyphenyl)methyl]-3,3a,4,6-tetrahydropyrrolo[3,4-c]isoxazol-6a-yl]-4-fluoro-phenyl]acetamide (5.0 g, 11.0 mmol) is added to water (75 mL), 10% palladium on carbon (2.5 g, 23 mmol), p-toluenesulfonic acid (5.0 g, 26 mmol), and ethanol (75 mL) and the mixture is hydrogenated under 50 psi hydrogen atmosphere at room temperature for 20 hours. The mixture is filtered through diatomaceous earth and the pad is washed with ethanol (100 mL) followed by DCM (100 mL). The filtrate is concentrated to give the title compound as a racemic cis mixture in quantitate crude yield (8.1 g, >100%). The material is used directly without further purification. ES/MS (m/z): 268 (M+H).

PREPARATION 12

((3R,4S)-1-Allyl-4-amino-4-(5-bromo-2-fluoro-phenyl)pyrrolidin-3-yl) methanol

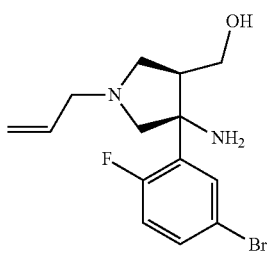 [SMILES: C=CCN1C[C@@H](CO)[C@](N)(c2cc(Br)ccc2F)C1]

1 N HCl (500 mL, 500 mmol) is added to a 0° C. solution of [(3S,4R)-1-allyl-3-(5-bromo-2-fluoro-phenyl)-4-(hydroxymethyl)pyrrolidin-3-yl]ammonium(2S,3S)-4-hydroxy-2,3-bis[(4-methylbenzoyl)oxy]-4-oxo-butanoate (100 g, 139.4 mmol) in EtOAc (500 mL). The mixture is stirred for 1 hour. The aqueous layer is separated and the pH is adjusted to 8 with 1 N NaOH. The aqueous layer is extracted with EtOAc (350 mL×2). The organic layers are combined, washed with water (500 mL) and concentrated to give the title compound (40 g, 87%). Chiral analysis of the second eluting isomer: Column: IC Chiralpak, 4.6 mm*250 mm*5 µm; eluent: 90% hexane (0.3% diethylamine): 10% ethanol (0.3% diethylamine); flow rate of 1.0 mL/min at UV 270 nm confirms the enantiomerically enriched (99.7% ee) enantiomer with $R_t$=7.4 minutes. $^1$H NMR (400 MHz, CDCl$_3$) δ 2.78-2.70(m, 5H), 3.16-3.00(m, 3H), 3.87-3.75(m, 1H), 3.90-3.84(m, 1H), 5.24-5.11(m, 2H), 5.91-5.87(m, 1H), 6.95-6.91(m, 1H), 7.35-7.32(m, 1H), 7.67-7.65(m, 1H).

PREPARATION 13

Relative-N-[3-[(3S,4R)-3-Amino-1-(5-fluoropyrimidin-2-yl)-4-(hydroxymethyl)pyrrolidin-3-yl]-4-fluoro-phenyl]acetamide

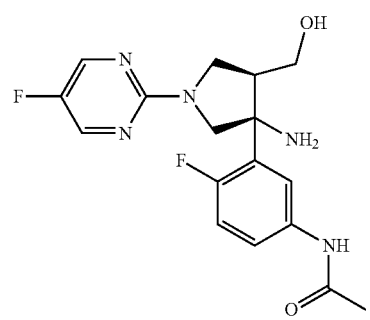 [SMILES: CC(=O)Nc1ccc(F)c([C@]2(N)CN(c3ncc(F)cn3)C[C@H]2CO)c1]

Relative-1-[3-[(3S,4R)-3-Amino-4-(hydroxymethyl)pyrrolidin-3-yl]-4-fluoro-phenyl]propan-2-one, di toluenesulfonic acid (7.5 grams, 12.3 mmol) is added to ACN (75 mL). 2-Chloro-5-fluoropyrimidine (2.44 g, 18.4 mmol) and DIPEA (7.5 mL, 43 mmol) are added and the mixture is heated to 70° C. for 20 hours. The mixture is cooled to room temperature and concentrated. Water (50 mL) is added the mixture is stirred for 1 hour as a slurry forms. The mixture is filtered and dried at room temperature under vacuum to give the title compound as a racemic cis mixture (3.0 g). The remaining aqueous solution is extracted with chloroform (3×20 mL), dried over sodium sulfate, concentrated to dryness and dried under vacuum to give additional title compound (1.8 g), for a total crude yield (4.8 g, 110%). ES/MS (m/z): 364 (M+H).

PREPARATION 14

N-(((3S,4R)-1-Allyl-3-(5-bromo-2-fluoro-phenyl)-4-(hydroxymethyl)pyrrolidin-3-yl)carbamothioyl)benzamide

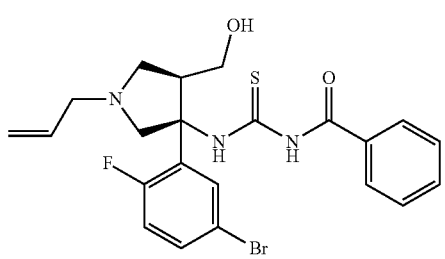 [SMILES: C=CCN1C[C@@H](CO)[C@](NC(=S)NC(=O)c2ccccc2)(c2cc(Br)ccc2F)C1]

Benzoyl isothiocyanate (15.0 g, 91.9 mmol) is added to a 0° C. solution of ((3R,4S)-1-allyl-4-amino-4-(5-bromo-2-fluoro-phenyl)pyrrolidin-3-yl)methanol (30 g, 91.1 mmol) in THF (400 mL). The solution is warmed to 25° C. and stirred for 1 hour to give a THF solution of the title compound, which is used without further purification.

PREPARATION 15

N-((4aR,7aS)-6-Allyl-7a-(5-bromo-2-fluoro-phenyl)-4,4a,5,7-tetrahydropyrrolo[3,4-d][1,3]thiazin-2-yl)benzamide, dihydrochloride

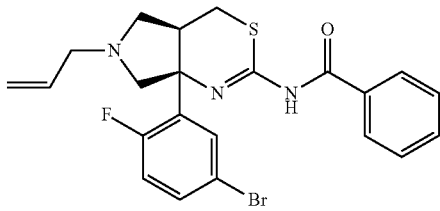 [SMILES: C=CCN1C[C@H]2CSC(NC(=O)c3ccccc3)=N[C@@]2(c2cc(Br)ccc2F)C1]

Triphenylphosphine (36.8 g, 140.3 mmol) is added to a THF (400 mL) solution of N-(((3S,4R)-1-allyl-3-(5-bromo-2-fluoro-phenyl)-4-(hydroxymethyl)pyrrolidin-3-yl)carbamothioyl)benzamide (91.1 mmol). Di-t-butyl azodicarboxylate (31.6 g, 137.2 mmol) in THF (100 mL) is added. The mixture is stirred at 20-30° C. for 2 hours. The mixture is concentrated and MTBE (400 mL) is added. The solution is filtered through diatomaceous earth and the cake is washed with MTBE (130 mL). The filtrates are combined and 1 N HCl in EtOAc (200 mL) is added. The mixture is stirred for 2 hours and then concentrated to 500 mL. MTBE (320 mL) is added and the solution is filtered and washed with heptane (130 mL). The solid is slurried in EtOAc (650 mL) and stirred at 50-60° C. for 2 hours The hot slurry is filtered and the solid is washed with EtOAc (130 mL) and heptane (130 mL). The solid is reslurried in EtOAc (650 mL) and stirred for 2 hours at 50-60° C. The hot slurry is filtered and washed with EtOAc (130 mL) and heptane (130 mL). The solid is dried to give the title compound as the di-HCl salt (40 g, 80%, 99.5% ee). Chiral analysis of the first eluting isomer: Column: IC Chiralpak, 4.6 mm*250 mm*5 μm; eluent: 85% hexane (0.1% diethylamine): 15% isopropyl alcohol (0.1% diethylamine); flow rate of 1.0 mL/min at UV 282 nm confirms the enantiomerically enriched (99.5% ee) enantiomer with $R_f$=12.5 minutes.

PREPARATION 16

N-[(4aR,7aS)-6-Allyl-7a-[2-fluoro-5-[(2,2,2-trifluoroacetyl)amino]phenyl]-4,4a,5,7-tetrahydropyrrolo[3,4-d][1,3]thiazin-2-yl]benzamide

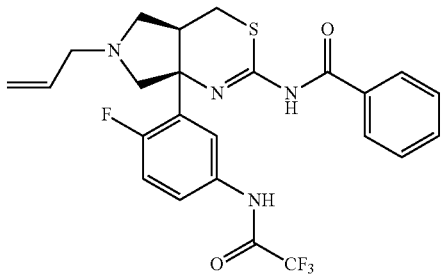 [SMILES: C=CCN1C[C@H]2CSC(NC(=O)c3ccccc3)=N[C@@]2(c2cc(NC(=O)C(F)(F)F)ccc2F)C1]

15% Sodium carbonate (440 mL) is added to a solution of N-((4aR,7aS)-6-Allyl-7a-(5-bromo-2-fluoro-phenyl)-4,4a,5,7-tetrahydropyrrolo[3,4-d][1,3]thiazin-2-yl)benzamide, dihydrochloride (495 g, 717.88 mmol) in EtOAc (3 L) and water (784 mL). The mixture is stirred for 1-2 hours. The layers are separated and the organic layer is filtered through silica gel (40 g) and washed with EtOAc (600 mL). The filtrate is concentrated to dryness to give N-((4aR,7aS)-6-allyl-7a-(5-bromo-2-fluoro-phenyl)-4,4a,5,7-tetrahydropyrrolo[3,4-d][1,3]thiazin-2-yl)benzamide. Trifluoroacetamide (136.7 g, 1.21 mol), NaI (182.5 g, 1.22 mol), 4 A molecular sieves (342 g), and $K_2CO_3$ (170.9 g, 1.24 mol) are added to a solution of N-((4aR,7aS)-6-allyl-7a-(5-bromo-2-fluoro-phenyl)-4,4a,5,7-tetrahydropyrrolo[3,4-d][1,3]thiazin-2-yl)benzamide (341 g, 494.54 mmol) in DMSO (525 mL) and 1,4-dioxane (1.025 L). Trans-N,N'-dimethylcyclohexane (81.6 g, 573.66 mmol) and copper iodide (27.3 g, 143.34 mmol) in DMSO (500 mL) are added to the reaction mixture. The mixture is stirred for 5 minutes. The mixture is warmed to 100° C. and stirred for 8 hours and cooled to 24° C. Water (5.9 L) and DCM (5.9 l) are added, the mixture is filtered, and the layers are separated. The organic layer is washed with water (5.9 L) to obtain the title compound in a solution of DCM, which is used without further purification.

PREPARATION 17

Relative-N-[(4aR,7aS)-7a-5-(Acetamido)-2-fluoro-phenyl)-6-(5-fluoropyrimidin-2-yl)-4,4a,5,7-tetrahydropyrrolo[3,4-d][1,3]thiazin-2-yl]benzamide

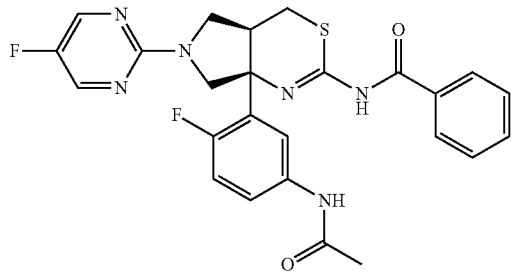 [SMILES: CC(=O)Nc1ccc(F)c([C@]23CN(c4ncc(F)cn4)C[C@H]2CSC(NC(=O)c2ccccc2)=N3)c1]

THF (30 mL) is added to relative-N-[3-[(3S,4R)-3-amino-1-(5-fluoropyrimidin-2-yl)-4-(hydroxymethyl)pyrrolidin-3-yl]-4-fluoro-phenyl]acetamide (4.1 g, 11.0 mmol). The mixture is cooled in an ice bath to 0° C. and benzoyl isothiocyanate (1.50 mL, 11.0 mmol) is added. The mixture is then allowed to warm room temperature over 30 minutes. 1,1'-Carbonyldiimidazole (1.9 g, 11.0 mmol) is added and the mixture is stirred at room temperature for 2 hours. The mixture is then heated to 55° C. and stirred an additional 18 hours. Water (50 mL) is added and the mixture is extracted with EtOAc (50 mL). The aqueous layer is extracted with additional EtOAc (25 mL) and concentrated to dryness. The crude residue is purified by silica gel flash column chromatography eluting with 50% DCM in EtOAc, followed by 100% EtOAc. The appropriate fractions are concentrated and dried under vacuum to give the title compound as a racemic cis mixture (1.33 g, 26%). ES/MS (m/z): 509 (M+H).

PREPARATION 18

N-((4aR,7aS)-6-Allyl-7a-(5-amino-2-fluoro-phenyl)-4,4a,5,7-tetrahydropyrrolo[3,4-d][1,3]thiazin-2-yl)benzamide, hydrochloride

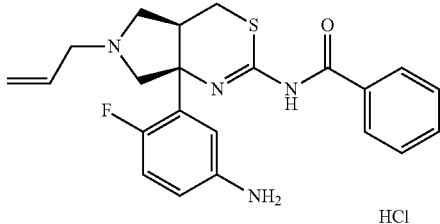 [SMILES: C=CCN1C[C@H]2CSC(NC(=O)c3ccccc3)=N[C@@]2(c2cc(N)ccc2F)C1 ; Cl]

HCl

NaOH (28.7 g) and water (2.7 L) are added to a DCM solution of N-[(4aR,7aS)-6-allyl-7a-[2-fluoro-5-[(2,2,2-trifluoroacetyl)amino]phenyl]-4,4a,5,7-tetrahydropyrrolo[3,4-d][1,3]thiazin-2-yl]benzamide (250 g, 494.4 mmol) and the mixture is stirred at 24° C. for 68 hours. 1 N HCl (3.5 L) is added to obtain a pH of 1-3. The layers are separated and the aqueous layer is washed with DCM (680 mL). DCM (4 L) is added to the aqueous followed by 21% ammonium hydroxide to obtain a pH of 8-10. The layers are separated and organic extracts are combined, filtered through silica gel (170 g) and washed with DCM (1.4 L). The solvent is concentrated to dryness and diluted with EtOAc (4 L). 1 N HCl in EtOAc (700 mL) is added at a temperature below 25° C. and the mixture is stirred for 1 hour. The mixture is concentrated to about 7-8 volumes and EtOAc (2.8 L) is added. The resulting precipitate is filtered and washed with EtOAc (400 mL). The solid is dried to give the title compound (246 g, 52%).

PREPARATION 19

N-((4aR,7aS)-7a-(5-Acetamido-2-fluoro-phenyl)-6-allyl-4,4a,5,7-tetrahydropyrrolo[3,4-d][1,3]thiazin-2-yl)benzamide

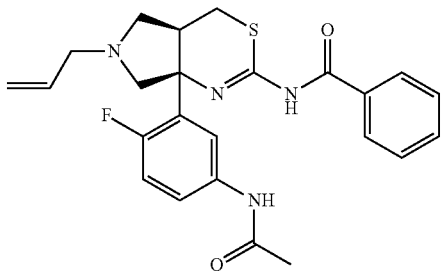 [SMILES: C=CCN1C[C@H]2CSC(NC(=O)c3ccccc3)=N[C@@]2(c2cc(NC(C)=O)ccc2F)C1]

Acetic anhydride (23.5 g, 0.23 mol) is added to a solution of N-((4aR,7aS)-6-allyl-7a-(5-amino-2-fluoro-phenyl)-4,4a,5,7-tetrahydropyrrolo[3,4-d][1,3]thiazin-2-yl)benzamide, hydrochloride (100 g, 0.153 mol) and triethylamine (54.3 g, 0.535 mol) in DCM (800 mL). After stirring for 1 hour at 20-25° C., saturated NaHCO₃ (700 mL) and water (600 mL) are added. The layers are separated to give the title compound, which is used without further purification as a solution in DCM.

PREPARATION 20

N-((4aR,7aS)-7a-(5-Acetamido-2-fluoro-phenyl)-4,4a,5,7-tetrahydropyrrolo[3,4-d][1,3]thiazin-2-yl)benzamide

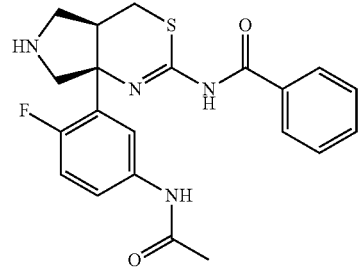 [SMILES: CC(=O)Nc1ccc(F)c([C@]23CNC[C@H]2CSC(NC(=O)c2ccccc2)=N3)c1]

Triphenylphosphine (4.0 g, 0.015 mol) and 1,3-dimethylbarbituric acid (15.2 g, 0.097 mol) are added to a DCM solution of N-((4aR,7aS)-7a-(5-acetamido-2-fluoro-phenyl)-6-allyl-4,4a,5,7-tetrahydropyrrolo[3,4-d][1,3]thiazin-2-yl)benzamide (0.153 mol). Palladium acetate (1.7 g, 7.7 mmol) is added and the mixture is stirred at 20 to 30° C. for 1 hour. 25% Ammonium hydroxide is added and the layers are separated. The organic layer is washed with HOAc (3.0 equiv in 500 mL of water) and the pH is adjusted to 8-9 with 25% ammonium hydroxide. The aqueous layer is extracted with DCM (2×500 mL). The organic extracts are combined and concentrated to 3-4 volumes. MTBE (1 L) is added and the mixture is filtered. The mixture is concentrated and heptane (1 L) is added. The resulting solid is filtered, collected, and dried to give the title compound (48 g, 76%). $^1$H NMR (400 MHz, CDCl₃) δ 2.15 (s, 3H), 2.87-2.83(m, 1H), 3.43-3.23(m, 5H), 3.70-3.67(m, 1H), 7.12-7.07 (m, 1H), 7.28-7.27 (m, 1H), 7.52-7.41(m, 4H), 7.79(m, 1H), 8.18-8.16(m, 2H), ES/MS (m/z): 413.1 (M+H).

PREPARATION 21

N-((4aR,7aS)-7a-(5-Acetamido-2-fluoro-phenyl)-6-(5-fluoropyrimidin-2-yl)-4,4a,5,7-tetrahydropyrrolo[3,4-d][1,3]thiazin-2-yl)benzamide

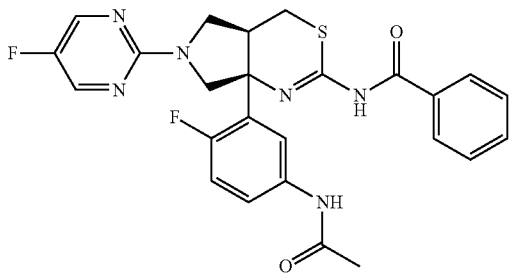 [SMILES: CC(=O)Nc1ccc(F)c([C@]23CN(c4ncc(F)cn4)C[C@H]2CSC(NC(=O)c2ccccc2)=N3)c1]

2-Chloro-5-fluoropyrimidine (28.9 g, 218 mmol) and potassium carbonate (33.46 g, 242.1 mmol) are added to a solution of N-((4aR,7aS)-7a-(5-acetamido-2-fluoro-phenyl)-4,4a,5,7-tetrahydropyrrolo[3,4-d][1,3]thiazin-2-yl)benzamide (50 g, 121.22 mmol) in DMF (100 mL). The mixture is heated to 80-85° C. for 8 hours. The mixture is cooled to 24° C., filtered, and washed with DMF (100 mL). The solids are slurried in water (2 L) and filtered to obtain the title compound (68.5 g, 98%). LC-MS: m/z=509.2 (M+H)+, $^1$H NMR (400 MHz, d$_6$-DMSO) δ ppm 1.22 (t, J=7.28 Hz, 2 H) 1.92-2.07 (m, 6 H) 2.89-3.20 (m, 2 H) 3.36-3.44 (m, 1 H) 3.67 (t, J=9.54 Hz, 1 H) 3.84 (br. s., 1 H) 4.16 (br. s., 2 H) 7.23 (br. s., 2 H) 7.35-7.61 (m, 8 H) 7.77 (br. s., 2 H) 7.85-8.18 (m, 4 H) 8.48 (s, 4 H) 10.15 (br. s., 1 H) 10.46-10.59 (m, 1 H).

PREPARATION 22

(4aR,7aS)-7a-(5-Amino-2-fluoro-phenyl)-6-(5-fluoropyrimidin-2-yl)-4,4a,5,7-tetrahydropyrrolo[3,4-d][1,3]thiazin-2-amine

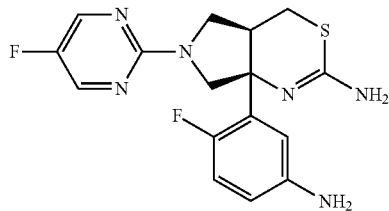 [SMILES: NC1=N[C@@]2(c3cc(N)ccc3F)CN(c3ncc(F)cn3)C[C@H]2CS1]

Lithium hydroxide (8.6 g, 204.9 mmol) is added to a solution of N-((4aR,7aS)-7a-(5-acetamido-2-fluoro-phenyl)-6-(5-fluoropyrimidin-2-yl)-4,4a,5,7-tetrahydropyrrolo[3,4-d][1,3]thiazin-2-yl)benzamide (80 g, 157.3 mmol) in methanol (400 mL). The mixture is heated to 60-70° C. for 4 hours. Concentrated HCl (132 g) is added and the mixture is stirred at 55° C. for 18 hours. The mixture is cooled to 30° C. and concentrated to remove the methanol. Water is added and the aqueous layer is extracted with DCM (3×) to obtain the title compound as an aqueous solution of 920 g of which 5.6% of the total mass is the title compound which is used without further purification.

ALTERNATE PREPARATION 22

Sulfuric acid (33.4 ml, 626.6 mmol) is added to a solution of (4aR,7aS)-7a-(2-fluorophenyl)-6-(5-fluoropyrimidin-2-yl)-4,4a,5,7-tetrahydropyrrolo[3,4-d][1,3]thiazin-2-amine (45.8 g, 125.3 mmol) in TFA (626 mL). The mixture is cooled to 0° C. and stirred for 20 minutes. Fuming nitric acid (6.2 mL, 144.1 mmol) is added and the reaction mixture is warmed to 22° C. and stirred at for 3 hours. The reaction mixture is evaporated and MTBE is added (250 mL) and evaporated twice. The residue is dried under vacuum to a constant weight and then is dissolved in water (147 mL) and ethanol (885 mL) and degassed with bubbling nitrogen for 15 minutes. The solution is transferred to a pressure reactor and 10% Pd/C paste type 87 L (6.6 g, 6.27 mmol) is added. The mixture is diluted with additional ethanol (700 mL) and pressurized with hydrogen at 80 psi for 16 hours. The reaction mixture is filtered and then a second catalyst charge is added of 10% Pd/C paste type 87 L (6.6 g, 6.27 mmol) and the mixture is pressurized to 80 psi and stirred for 3 days in the pressure reactor. The reaction mixture is purged with nitrogen and filtered over diatomaceous earth. The filtrate is evaporated and the residue is partitioned between water (200 ml) and EtOAc (200 ml). The aqueous layer is separated, cooled to 5° C., and neutralized with ammonium hydroxide 15% w/w. The aqueous layer is extracted with EtOAc (3×150 mL). The organics are combined, dried over sodium sulfate, filtered, and evaporated under reduced pressure to give the title compound as light brown solid (47.7 g, 99% containing residual EtOAc). ES/MS (m/z): 363 (M+H).

PREPARATION 23

Benzyl N-allyl-N-(2,2-dimethoxyethyl)carbamate

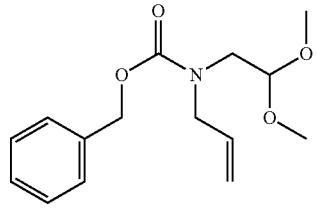 [SMILES: C=CCN(CC(OC)OC)C(=O)OCc1ccccc1]

A solution of benzyl N-(2,2-dimethoxyethyl)carbamate (50 g, 208.9 mmol) in toluene (180 mL) is treated with solid potassium hydroxide (51.6 g, 919.69 mmol) under nitrogen. After 10 minutes, benzyltriethylammonium chloride (0.8 g, 3.1 mmol) is added. After another 10 minutes a solution of allyl bromide (33 g, 272.8 mmol) in toluene (50 mL) is added dropwise over 10 minutes. The resultant mixture is stirred at 50° C. for 48 hours. The mixture is cooled to room temperature and quenched with water. The organic layer is separated, washed with brine, dried over magnesium sulfate, and concentrated to dryness to give the title compound (44 g, 75%). ES/MS (m/z): 280 (M+H).

PREPARATION 24

Benzyl N-allyl-N-(2-oxoethyl)carbamate

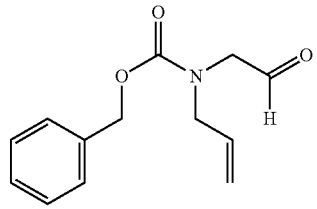 [SMILES: C=CCN(CC=O)C(=O)OCc1ccccc1]

A solution of benzyl N-allyl-N-(2,2-dimethoxyethyl)carbamate (30 g, 107 mmol) in formic acid (36.8 mL, 860 mmol) and water (4.84 mL) is stirred at room temperature overnight. The mixture is concentrated and diluted with hexanes/EtOAc (1:2) and water. The organic layer is separated, washed with brine solution until pH=6, and dried over sodium sulfate. The solvent is evaporated to give the title compound (25 g, 99%). ES/MS (m/z): 234 (M+H).

PREPARATION 25

Benzyl N-allyl-N-[2-hydroxyiminoethyl]carbamate

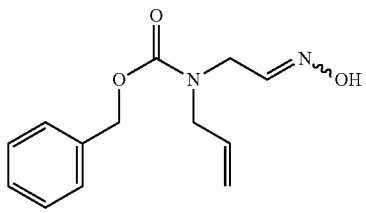 [SMILES: C=CCN(CC=NO)C(=O)OCc1ccccc1]

A solution of benzyl N-allyl-N-(2-oxoethyl)carbamate (25 g, 107 mmol) in ACN (150 mL) is treated with hydroxylamine hydrochloride (9.68 g, 139 mmol) and a solution of sodium acetate trihydrate (16 g, 117.9 mmol) in water (75 mL). The mixture is stirred at room temperature overnight. The ACN is evaporated and the aqueous solution is extracted with EtOAc. The organic layer is separated, dried over magnesium sulfate, and concentrated under vacuum to give the title compound (24 g, 90%). ES/MS (m/e): 249 (M+H).

PREPARATION 26

Benzyl 3,3a,4,6-tetrahydropyrrolo[3,4-c]isoxazole-5-carboxylate

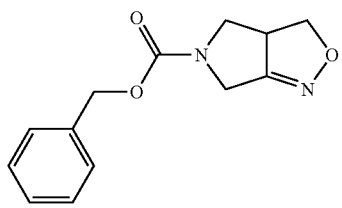 [SMILES: O=C(OCc1ccccc1)N1CC2=NOCC2C1]

A solution of benzyl N-allyl-N-[2-hydroxyiminoethyl]carbamate (24 g, 96.6 mmol) in DCM (338 mL) is treated dropwise over 10 minutes with a 5% w/w aqueous solution of sodium hypochlorite (106.08 mmol, 143.06 mL). The resultant mixture is stirred at room temperature overnight. The reaction is quenched with a 40% aqueous solution of sodium bisulfite (7 g). The organic layer is separated, dried over magnesium sulfate, and concentrated under vacuum. The crude product is purified over silica gel eluting with 5% EtOAc in hexanes to give the title compound (18 g, 75%). ES/MS (m/z): 247 (M+H).

PREPARATION 27

Benzyl 6a-(5-bromo-2-fluoro-phenyl)-3,3a,4,6-tetrahydro-1H-pyrrolo[3,4-c]isoxazole-5-carboxylate

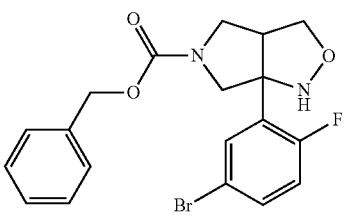 [SMILES: O=C(OCc1ccccc1)N1CC2CONC2(c2cc(Br)ccc2F)C1]

A 1.6 M hexanes solution of n-butyl lithium (25.4 mL, 40.6 mmol) is added dropwise to a −78° C. solution of 4-bromo-1-fluoro-2-iodobenzene (12.22 g, 40.6 mmol) in THF (60 mL) to give a yellow solution that is stirred at −78° C. for 15 minutes. Boron trifluoride etherate (5.14 mL, 40.6 mmol) is added to a separate −78° C. solution of benzyl 3,3a,4,6-tetrahydropyrrolo[3,4-c]isoxazole-5-carboxylate (5 g, 20.3 mmol) in THF (60 mL) and the mixture is stirred at −78° C. for 5 minutes. This solution is added to the previously prepared −78° C. organolithium mixture via cannula. The combined mixture is stirred for 30 minutes at −78° C. The mixture is quenched with saturated aqueous ammonium chloride and warmed to room temperature. The mixture is extracted with EtOAc (3×) and the organic extracts are combined, dried over sodium sulfate, filtered and the solvent removed in vacuo. The crude product is purified over silica gel with a 35 minute 5% to 100% EtOAc in hexanes gradient to give the title compound (2.27 g, 27%). ES/MS (m/z): ($^{79}$Br/$^{81}$Br) 421/423 (M+H).

PREPARATION 28

Benzyl 1-(benzoylcarbamothioyl)-6a-(5-bromo-2-fluoro-phenyl)-3,3a,4,6-tetrahydropyrrolo[3,4-c]isoxazole-5-carboxylate

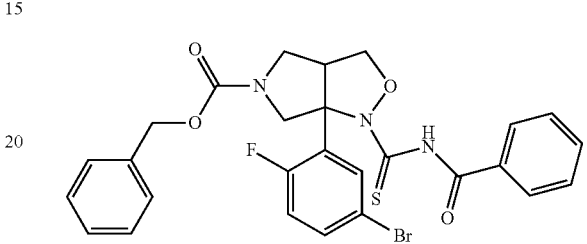

Benzoyl isothiocyanate (2.87 mL, 21.28 mmol) is added dropwise to a solution of benzyl 6a-(5-bromo-2-fluoro-phenyl)-3,3a,4,6-tetrahydro-1H-pyrrolo[3,4-c]isoxazole-5-carboxylate (5.977 g, 14.2 mmol) in THF (95 mL) and stirred overnight under nitrogen. The solvent is removed in vacuo. The crude product is purified over silica gel with a 30 minute 5% to 100% EtOAc in hexanes gradient to give the title compound (6.05 g, 73%). ES/MS (m/z): ($^{79}$Br/$^{81}$Br) 584/586 (M+H).

PREPARATION 29

Benzyl 3-(benzoylcarbamothioylamino)-3-(5-bromo-2-fluoro-phenyl)-4-(hydroxymethyl)pyrrolidine-1-carboxylate

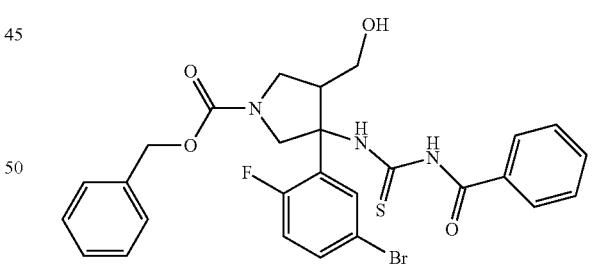

A mixture of benzyl 1-(benzoylcarbamothioyl)-6a-(5-bromo-2-fluoro-phenyl)-3,3a,4,6-tetrahydropyrrolo[3,4-c]isoxazole-5-carboxylate (6.05 g 10.4 mmol) and zinc (dust, <10 micron) (6.77 g, 103.5 mmol) is stirred in HOAc (52 mL) at room temperature overnight under nitrogen. The reaction is diluted with EtOAc and filtered through diatomaceous earth. The solvent is removed in vacuo and the residue is diluted with EtOAc, water, and saturated aqueous sodium bicarbonate. The mixture is extracted with EtOAc (3×), the combined organic layers are combined and dried over sodium sulfate, filtered, and the solvent removed in vacuo. The crude product is purified over silica gel with a 30 minute 5% to 100% EtOAc in hexanes gradient to give the title compound (5.222 g, 86%). ES/MS (m/z): ($^{79}$Br/$^{81}$Br) 586/588 (M+H).

PREPARATION 30

Benzyl 2-benzamido-7a-(5-bromo-2-fluoro-phenyl)-4,4a,5,7-tetrahydropyrrolo[3,4-d][1,3]thiazine-6-carboxylate

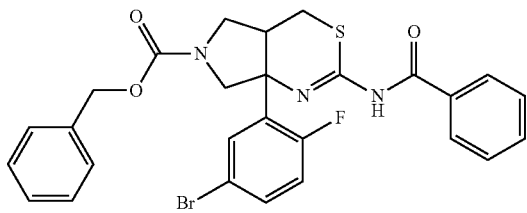 [SMILES: O=C(NC1=NC2(c3cc(Br)ccc3F)CN(C(=O)OCc3ccccc3)CC2CS1)c1ccccc1]

1,1'-carbonyldiimidazole (2.87 g, 17.7 mmol) is added to a solution of benzyl 3-(benzoylcarbamothioylamino)-3-(5-bromo-2-fluoro-phenyl)-4-(hydroxymethyl)pyrrolidine-1-carboxylate (5.198 g, 8.86 mmol) in THF (52 mL). The mixture is stirred for 1.5 hours at room temperature and then the reaction is heated at reflux overnight under nitrogen. The reaction is cooled, diluted with water, and extracted with EtOAc (3×). The organic layers are combined, dried over sodium sulfate, filtered, and the solvent removed in vacuo. The crude product is purified over silica gel with a 30 minute 5% to 100% EtOAc in hexanes gradient to give the title compound (2.93 g, 58%). ES/MS (m/z): ($^{79}$Br/$^{81}$Br). 568/570 (M+H)

PREPARATION 31

N-[7a-(5-Bromo-2-fluoro-phenyl)-4a,5,6,7-tetrahydro-4H-pyrrolo[3,4-d][1,3]thiazin-2-yl]benzamide

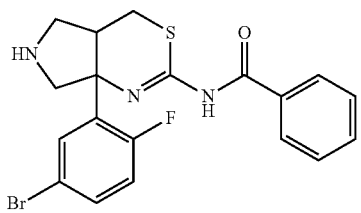 [SMILES: O=C(NC1=NC2(c3cc(Br)ccc3F)CNCC2CS1)c1ccccc1]

Iodotrimethylsilane (2.21 mL, 15.46 mmol) is added dropwise to a room temperature solution of benzyl 2-benzamido-7a-(5-bromo-2-fluoro-phenyl)-4,4a,5,7-tetrahydropyrrolo[3,4-d][1,3]thiazine-6-carboxylate (2.93 g, 5.15 mmol) in ACN (44 mL). The reaction is stirred at room temperature for two hours and the solvent is removed in vacuo. The crude product is purified with an SCX column using 3:1 DCM:methanol and then 2:1 DCM:7 N ammonia in methanol to give the title compound (2.098 g, 94%). ES/MS (m/z): ($^{79}$Br/$^{81}$Br) 434/436 (M+H).

PREPARATION 32 tert-Butyl 2-benzamido-7a-(5-bromo-2-fluoro-phenyl)-4,4a,5,7-tetrahydropyrrolo[3,4-d][1,3]thiazine-6-carboxylate

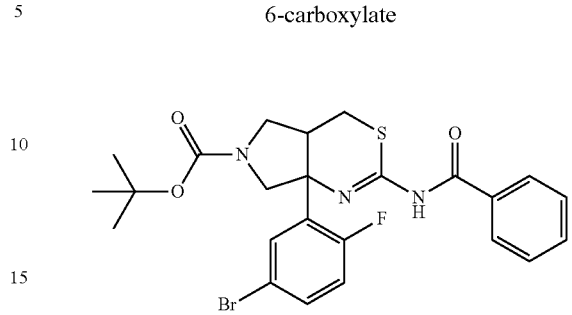

Di-t-butyldicarbonate (1.16 g, 5.31 mmol) and triethylamine (1.01 mL, 7.25 mmol) are added to a solution of N-[7a-(5-bromo-2-fluoro-phenyl)-4a,5,6,7-tetrahydro-4H-pyrrolo[3,4-d][1,3]thiazin-2-yl]benzamide (2.098 g, 4.83 mmol) in DCM (48 mL). The reaction is stirred for 1 hour at room temperature under nitrogen. The solvent is removed in vacuo and the crude product is purified over silica gel with a 30 minute 5% to 100% EtOAc in hexanes gradient to give the title compound (2.556 g, 99%). ES/MS (m/z): ($^{79}$Br/$^{81}$Br) 534/536 (M+H).

PREPARATION 33 tert-Butyl 7a-(5-amino-2-fluoro-phenyl)-2-benzamido-4,4a,5,7-tetrahydropyrrolo[3,4-d][1,3]thiazine-6-carboxylate

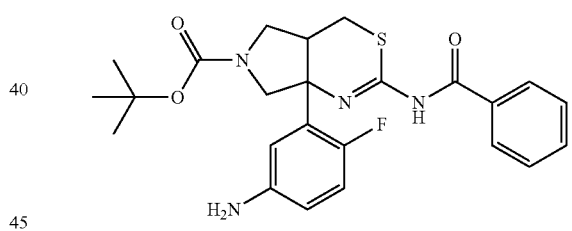

A solution of tert-butyl 2-benzamido-7a-(5-bromo-2-fluoro-phenyl)-4,4a,5,7-tetrahydropyrrolo[3,4-d][1,3]thiazine-6-carboxylate (2.556 g, 4.8 mmol) and trans-N,N'-dimethyl-1,2-cyclohexanediamine (150 mg, 1.1 mmol) in ethanol (50 mL) is treated with sodium azide (933 mg, 14.3 mmol). An aqueous solution of L-ascorbic acid sodium salt (0.66 M, 3.2 mL, 2.1 mmol) and water (1 mL) are added and the top of the flask is purged with nitrogen. The mixture is treated with an aqueous solution of copper(II)sulfate pentahydrate (0.33 M, 3.2 mL, 1.1 mmol) and the mixture is immediately heated on a preheated hot plate at 80° C. for 1.5 hours under nitrogen. A homogeneous mixture is obtained upon heating. The reaction is cooled, diluted with ice water, and the mixture is extracted with EtOAc (3×). The organic extracts are combined and dried over sodium sulfate, filtered, and the solvent removed in vacuo to give the crude azide product. The crude azide product is combined with 10% palladium on carbon (1 g) in cold ethanol (150 mL) and the mixture is purged using vacuum/nitrogen and then vacuum/hydrogen. The mixture is stirred at room temperature under 30 psi of hydrogen for 5 hours. The reaction is vented, filtered through diatomaceous earth, and the filter cake rinsed with DCM. The solvent is removed from the filtrate in vacuo and the crude product is purified over silica gel with 50% EtOAc in DCM to give the title compound (2.014 g, 89%). ES/MS (m/z): 471 (M+H).

PREPARATION 34

N-[7a-(5-Amino-2-fluoro-phenyl)-4a,5,6,7-tetra-hydro-4H-pyrrolo[3,4-d][1,3]thiazin-2-yl]benzamide

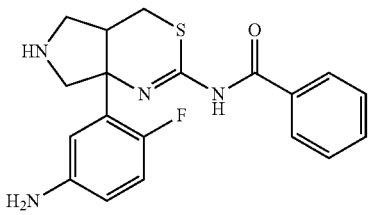 [SMILES: Nc1ccc(F)c(C23CNCC2CSC(NC(=O)c2ccccc2)=N3)c1]

TFA (10 mL) is added to a solution of tert-butyl 7a-(5-amino-2-fluoro-phenyl)-2-benzamido-4,4a,5,7-tetrahydropyrrolo[3,4-d][1,3]thiazine-6-carboxylate (2.013 g, 4.28 mmol) in DCM (30 mL) and the mixture is stirred at room temperature under nitrogen for 4 hours. The solvent removed in vacuo and the crude product is purified with an SCX column using 3:1 DCM:methanol and then 2:1 DCM:7 N ammonia in methanol to give the title compound (1.555 g, 98%). ES/MS (m/z): 371 (M+H).

PREPARATION 35

Racemic N-[7a-(5-Amino-2-fluoro-phenyl)-6-(5-fluoropyrimidin-2-yl)-4,4a,5,7-tetrahydropyrrolo[3,4-d][1,3]thiazin-2-yl]benzamide

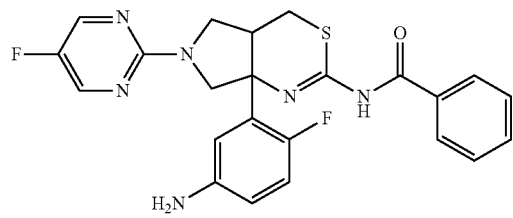 [SMILES: Nc1ccc(F)c(C23CN(c4ncc(F)cn4)CC2CSC(NC(=O)c2ccccc2)=N3)c1]

A solution of N-[7a-(5-amino-2-fluoro-phenyl)-4a,5,6,7-tetrahydro-4H-pyrrolo[3,4-d][1,3]thiazin-2-yl]benzamide (705 mg, 1.90 mmol), 5-fluoro-2-chloropyrimidine (1.01 g, 7.61 mmol), and DIPEA (1.66 mL, 9.52 mmol) are heated in 1,4-dioxane (20 mL) to reflux for 4 hours under nitrogen. The reaction is cooled, diluted with water, and extracted with EtOAc (3×). The organic layers are combined, dried over sodium sulfate, filtered and the solvent removed in vacuo to give crude product. The crude product is purified over silica gel with a 25 minute 5% to 100% EtOAc in hexanes gradient to give the title compound (590 mg, 66%). ES/MS (m/z): 467 (M+H).

PREPARATION 36

N-[(4aR,7aS)-7a-(5-Amino-2-fluoro-phenyl)-6-(5-fluoropyrimidin-2-yl)-4,4a,5,7-tetrahydropyrrolo[3,4-d][1,3]thiazin-2-yl]benzamide, (Isomer 1)

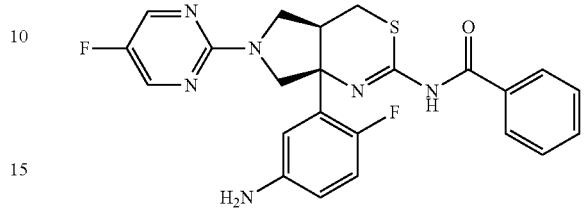

Racemic N-[7a-(5-amino-2-fluoro-phenyl)-6-(5-fluoropyrimidin-2-yl)-4,4a,5,7-tetrahydropyrrolo[3,4-d][1,3]thiazin-2-yl]benzamide (1.694 g, 3.63 mmol) is purified by chiral HPLC (Column: Chiralcel OJ, 8×35 cm; eluent: 90% methanol (0.2% dimethylethylamine) and 10% ACN; flow 400 mL/min at UV 280 nm). Analysis of the first eluting isomer (Column: Chiralcel OJ-H 0.46×15 cm; eluent: 10:90 ACN:methanol (with 0.2% dimethylethylamine); flow: 0.6 mL/min at UV 280 nm) confirms the enantiomerically enriched (99% ee) enantiomer with $R_t$=6.70 minutes, (723 mg, 43%). ES/MS (m/z): 467 (M+H).

PREPARATION 37

N-[3-[(4aR,7aS)-2-Benzamido-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide, Isomer 1

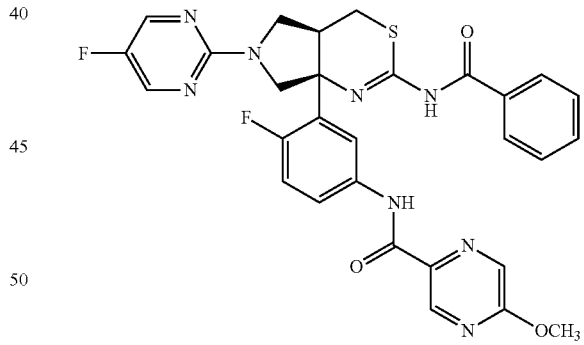

N-[(4aR,7aS)-7a-(5-Amino-2-fluoro-phenyl)-6-(5-fluoropyrimidin-2-yl)-4,4a,5,7-tetrahydropyrrolo[3,4-d][1,3]thiazin-2-yl]benzamide, isomer 1 (0.361 g, 0.77 mmol) is dissolved in a mixture of DCM (4 mL) and DMF (0.5 mL). 5-Methoxypyrazine-2-carboxylic acid (240 mg, 1.55 mmol), HOBT (210 mg, 1.55 mmol) and EDCI (300 mg, 1.55 mmol) are added to the mixture and the mixture is stirred overnight at room temperature. The reaction solution is added directly onto a 12 g silica gel loading column and purified using a 40 g silica gel column and eluting with a 0-100% EtOAc/hexanes gradient. The product is dissolved in EtOAc (200 mL), washed with 1 N NaOH (2×50 mL), and with brine (1×50 mL). The silica gel purification is repeated as described above to give the title compound (350 mg, 74%). ES/MS (m/z): 603 (M+H).

PREPARATION 38

5-Allyl-6a-(2-fluorophenyl)-3,3a,4,6-tetrahydro-1H-pyrrolo[3,4-c]isoxazole

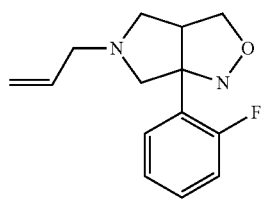 [SMILES: C=CCN1CC2CONC2(c2ccccc2F)C1]

Flow chemistry reaction step: A 343-ml seamless stainless steel tubular reactor (OD=⅛ inch) is placed inside a GC oven and flushed with toluene at 20 mL/min for 20 minutes. Apply back pressure of nitrogen (720 psig) and set the temperature of the GC to 210° C. After the temperature has reached 210° C., a solution of 2-(diallylamino)-1-(2-fluorophenyl)ethanone oxime (480.51 g, 1.74 mol) in toluene (5.81 L) is pumped through the reactor at 22.866 mL/min using a pair of high-pressure syringe pumps working in continuous mode to give a residence time of 15 minutes. After all the stock solution is consumed the reactor is flushed with toluene at 22.866 mL/min for 30 minutes. The temperature of the GC oven is set to 25° C. and the complete solution is collected and concentrated under vacuum. The solvent is evaporated and residue dissolved in DCM (2.5 L) and water (5 L). The pH is adjusted to 1 with HCl and the aqueous layer is separated and neutralized with NaOH to adjust the pH to 10. The aqueous layer is extracted with MTBE (3×2.5 L). The organic extracts are combined, dried over sodium sulfate, filtered, and evaporated to dryness to give the crude title compound (248 g, 47%) which is used without further purification. ES/MS (m/z): 249 (M+H).

PREPARATION 39

1-Allyl-4-amino-4-(2-fluorophenyl)pyrrolidin-3-yl]methanol

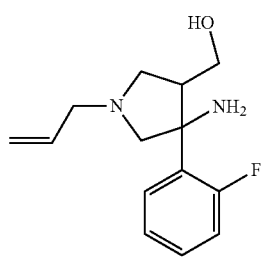 [SMILES: C=CCN1CC(CO)C(N)(c2ccccc2F)C1]

Zinc dust (590 g, 9 mol) is added to a solution of 5-allyl-6a-(2-fluorophenyl)-3,3a,4,6-tetrahydro-1H-pyrrolo[3,4-c]isoxazole (3559 g, 1.29 mol) in a mixture of methanol (2.85 L) and ammonium chloride saturated aqueous solution (3.56 L) and mixture is heated for 16 hours at 70° C. The reaction is cooled to 60° C., diluted with THF (2.85 L), and filtered while hot over diatomaceous earth. The filtrate is evaporated to remove the organic solvent, and the aqueous mixture is diluted with citric acid 10% w/w aqueous solution (4 L) and EtOAc (3.5 L). The organic layer is separated and the aqueous layer washed with EtOAc (2×2 L). The aqueous layer is neutralized with NaOH 50% w/w to adjust the pH to 10, and then is extracted with EtOAc (2×1.5 L). The organic extracts are combined, dried over sodium sulfate, filtered, and evaporated to dryness to give the crude title compound (299 g, 92%). ES/MS (m/z): 251 (M+H).

PREPARATION 40

[(3R,4S)-1-Allyl-4-amino-4-(2-fluorophenyl)pyrrolidin-3-yl]methanol; 2,3-bis[(4-methylbenzoyl)oxy]butanedioic acid

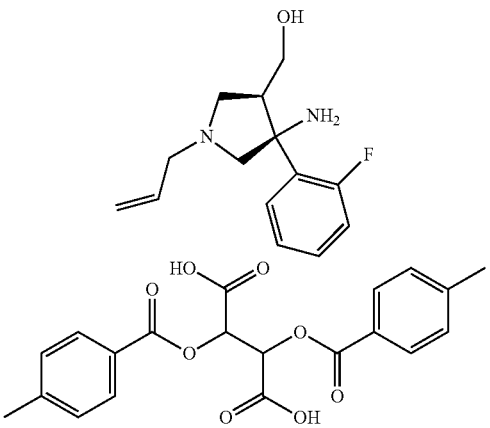

A solution of di-p-toluoyl-L-tartaric acid (348.6 g, 884 mmol) in 1-methoxy-2-propanol (1.13 L) is added to a solution of [(3R,4S)-1-allyl-4-amino-4-(2-fluorophenyl)pyrrolidin-3-yl]methanol (225.9 g, 902 mmol), in 1-methoxy-2-propanol (1.13 L) previously heated at 40° C. The reaction is cooled to 22° C. and stirred for 18 hours. A white solid is collected by filtration and washed with 1-methoxy-2-propanol (600 ml). The collected solid is dried to give the title compound (183.01 g, 31.8%). ES/MS (m/z): 251 (M+H).

PREPARATION 41

[(3R,4S)-1-Allyl-4-amino-4-(2-fluorophenyl)pyrrolidin-3-yl]methanol

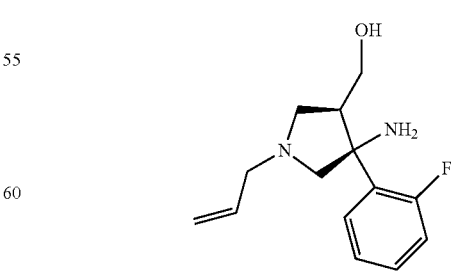

[(3R,4S)-1-Allyl-4-amino-4-(2-fluorophenyl)pyrrolidin-3-yl]methanol; 2,3-bis[(4-methylbenzoyl)oxy]butanedioic acid (211 g, 331 mmol) is dissolved in water (2.1 L) and EtOAc (2.3 L). HCl 35% w/w is added to adjust the pH to 1. The aqueous layer is separated and the pH adjusted to 10 with NaOH 50% w/w and extracted with EtOAc (2×). The pH of the aqueous layer is adjusted to 10 with aqueous NaOH, and extracted with MTBE (3×) while also maintaining the pH of the aqueous solution at pH=10. The organic extracts are combined, dried over sodium sulfate, filtered, and concentrated to dryness to give the crude title compound, (73 g, 88%, 94.8% ee). The product is analyzed by chiral chromatography: Column AS-H, eluent 10% isopropyl alcohol, 2% isopropyl amine; flow rate of 3 mL/min at UV 220; pressure of 100 bar at 35° C. to give the title compound as the second eluting isomer, R$_f$=2.26 minutes. ES/MS (m/z): 251 (M+H).

PREPARATION 42

N-[(4aR,7aS)-6-Allyl-7a-(2-fluorophenyl)-4,4a,5,7-tetrahydropyrrolo[3,4-d][1,3]thiazin-2-yl]benzamide

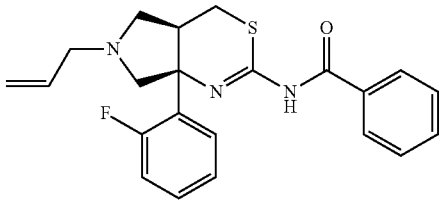 [SMILES: C=CCN1C[C@H]2CSC(NC(=O)c3ccccc3)=N[C@@]2(c2ccccc2F)C1]

A solution of [(3R,4S)-1-allyl-4-amino-4-(2-fluorophenyl)pyrrolidin-3-yl]methanol (129.7 g, 414 mmol) in THF (2.3 L) is cooled at 0° C. under a nitrogen atmosphere. Benzoyl isothiocyanate (61.5 mL, 456 mmol) is added keeping the temperature below 5° C. The reaction is warmed to room temperature over 3 hours and 1,1'-carbonyldiimidazole (87.4 g, 538.9 mmol) is added and the reaction stirred at 22° C. for 1 hour followed by heating at 70° C. for 16 hours. The reaction mixture is cooled to 22° C. and the solvent is evaporated. The residue is partitioned in EtOAc (1 L) and water (1 L). The organic layer is separated and the aqueous layer is extracted with EtOAc (2×400 mL). The organics are combined, dried over sodium sulfate, filtered, and evaporated to dryness to give the crude title compound. The crude product is purified by silica gel chromatography eluting with a gradient of EtOAc/DCM from 0-40% DCM to give the title compound as pale yellow solid (170 g, 99%) containing residual solvent. ES/MS (m/z): 396 (M+H).

PREPARATION 43

N-[(4aR,7aS)-7a-(2-Fluorophenyl)-4a,5,6,7-tetrahydro-4H-pyrrolo[3,4-d][1,3]thiazin-2-yl]benzamide

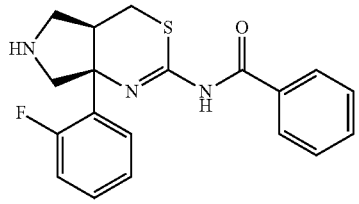 [SMILES: O=C(NC1=N[C@@]2(c3ccccc3F)CNC[C@H]2CS1)c1ccccc1]

Benzoic Acid, 2-mercapto—(122 g, 793 mmol), bis (dibenzylideneacetone)palladium (4.15 g, 7.21 mmol), and 1,4-bis(diphenylphosphino)butane (3.14 g, 7.21 mmol) are added to a solution of N-[(4aR,7aS)-6-allyl-7a-(2-fluorophenyl)-4,4a,5,7-tetrahydropyrrolo[3,4-d][1,3]thiazin-2-yl]benzamide (178.21 g, 360 mmol) in anhydrous 2-methyltetrahydrofuran (1.96 L) under a nitrogen atmosphere. The solution is degassed by vacuum/nitrogen cycles three times, and then nitrogen is bubbled through the reaction for 15 minutes. The reaction mixture is heated to 40° C. while bubbling nitrogen through the reaction. When reaction reaches 40° C. the bubbling is removed and reaction mixture is stirred at 40° C. for 3 hours under a nitrogen atmosphere. The reaction is cooled to 22° C. and diluted with water (2 L). HCl (5 M) solution is added to adjust the pH to 1. The aqueous layer is separated and washed with additional EtOAc (2×800 mL). The pH of the aqueous layer is adjusted to 10 with NaOH 50% w/w and then is extracted with EtOAc (10 L). The aqueous layer is washed with additional EtOAc (2×750 mL). The organic extracts are combined, washed with brine, dried over sodium sulfate, filtered, and evaporated to dryness to give the crude title compound as pale yellow solid (124.7 g, 97%). ES/MS (m/z): 356 (M+H).

PREPARATION 44

N-[(4aR,7aS)-7a-(2-Fluorophenyl)-6-(5-fluoropyrimidin-2-yl)-4,4a,5,7-tetrahydropyrrolo[3,4-d][1,3]thiazin-2-yl]benzamide

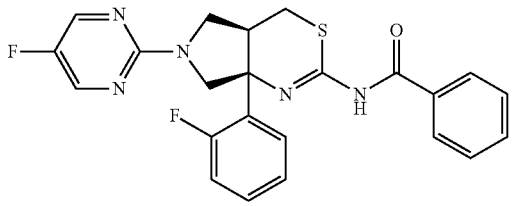 [SMILES: O=C(NC1=N[C@@]2(c3ccccc3F)CN(c3ncc(F)cn3)C[C@H]2CS1)c1ccccc1]

A solution of N-[(4aR,7aS)-7a-(2-fluorophenyl)-4a,5,6,7-tetrahydro-4H-pyrrolo[3,4-d][1,3]thiazin-2-yl]benzamide (124.7 g, 256 mmol), DIPEA (67 mL), 5-fluoro-2-chloropyrimidine (29.3 ml, 307 mmol) in N-methylpyrrolidone (997 mL) is heated to 100° C. for 16 hours. The reaction is cooled to 22° C. and poured into cooled water at 10° C. (10 L) keeping temperature below 15° C. A pale cream solid is collected by filtration and washed with additional water. The wet solid is dissolved in EtOAc (2 L) and transferred to a separator funnel. Sodium chloride aqueous solution 5% w/w (1 L) is added and the organic layer is separated, dried over sodium sulfate, filtered, and the filtrate evaporated under reduced pressure. The product is purified by silica gel chromatography using a gradient of 0-40% EtOAc/isohexane to give the title compound as a pale yellow solid (116 g, 70%). ES/MS (m/z): 452 (M+H).

PREPARATION 45

(4aR,7aS)-7a-(2-Fluorophenyl)-6-(5-fluoropyrimidin-2-yl)-4,4a,5,7-tetrahydropyrrolo[3,4-d][1,3]thiazin-2-amine

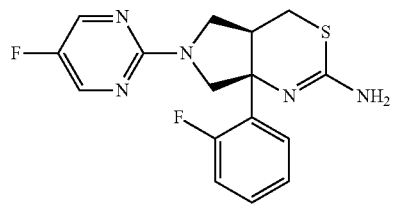 [SMILES: NC1=N[C@@]2(c3ccccc3F)CN(c3ncc(F)cn3)C[C@H]2CS1]

Lithium hydroxide (9.26 g, 386 mmol) is added to a mixture of N-[(4aR,7aS)-7a-(2-fluorophenyl)-6-(5-fluoro-pyrimidin-2-yl)-4,4a,5,7-tetrahydropyrrolo[3,4-d][1,3]thiazin-2-yl]benzamide (158.6 g, 351.6 mmol), in methanol (1.6 L). The mixture is heated at 70° C. for 4 hours and then cooled to 22° C. The reaction mixture is evaporated under vacuum to a yellow residue. The residue is partitioned in water (1 L) and EtOAc (750 mL). HCl (5 M aqueous solution) is added to adjust the pH to 1. The aqueous layer is separated and the organic layer is washed with EtOAc (2×200 mL). The pH of the aqueous layer is adjusted with NaOH 50% w/w aqueous solution to pH=10 and extracted with EtOAc (3×1 L). The organic extracts are combined, dried over sodium sulfate, filtered, and evaporated under reduced pressure to give crude title compound as a pale yellow solid (133.3 g, 99%, containing 12% residual EtOAc). ES/MS (m/z): 348 (M+H).

PREPARATION 46

N-[3-[(4aR,7aS)-2-Amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide hydrochloride

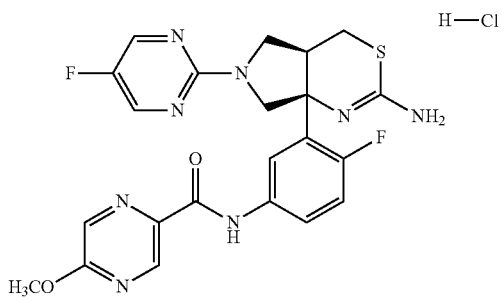 [SMILES: Cl ; COc1cnc(C(=O)Nc2ccc(F)c([C@]34CN(c5ncc(F)cn5)C[C@H]3CSC(N)=N4)c2)cn1]

N-[3-[(4aR,7aS)-2-Benzamido-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide, isomer 1 (0.350 g, 0.58 mmol) is dissolved in THF (2 mL) and then methanol (4 mL) and ethanol (4 mL) are added. O-Methyl-hydroxylamine hydrochloride (495 mg, 5.81 mmol) and pyridine (470 µL, 5.81 mmol) are added to the mixture and the reaction is warmed to 50° C. and stirred overnight. Silica gel (~10 g) is added to the reaction and the mixture is concentrated. The sample, dried onto silica gel, is loaded onto an empty cartridge and purified eluting with a 0-10% gradient of 7 N ammonia methanol in DCM. The product is purified a second time on a SCX column using 3:1 DCM: methanol and then 2:1 DCM:7 N ammonia in methanol. The product is purified a final time over silica gel with a 0% to 10% gradient of 7 N ammonia methanol in DCM to give the free base of the title compound. This material is dissolved in DCM (5 mL) and 1 M HCl in diethyl ether (0.20 mL, 660 µmol) is added. The solvent is removed in vacuo to give the title compound (71 mg, 23%). ES/MS (m/z): 498 (M+H).

X-Ray Powder Diffraction (XRD)

The XRD patterns of crystalline solids are obtained on a Bruker D4 Endeavor X-ray powder diffractometer, equipped with a CuKa source λ=1.54060 Å) and a Vantec detector, operating at 35 kV and 50 mA. The sample is scanned between 4 and 40° in 2θ, with a step size of 0.009° in 2θ and a scan rate of 0.5 seconds/step, and with 0.6 mm divergence, 5.28 fixed anti-scatter, and 9.5 mm detector slits. The dry powder is packed on a quartz sample holder and a smooth surface is obtained using a glass slide. The crystal form diffraction patterns are collected at ambient temperature and relative humidity. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g., The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2 in 2θ will take into account these potential variations without hindering the unequivocal identification of the indicated crystal form. Confirmation of a crystal form may be made based on any unique combination of distinguishing peaks (in units of ° 2θ), typically the more prominent peaks. The crystal form diffraction patterns, collected at ambient temperature and relative humidity, are adjusted based on NIST 675 standard peaks at 8.853 and 26.774 degrees 2-theta.

PREPARATION 47

Crystalline Form 2 N-[3-[(4aR,7aS)-2-Amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide (Hydrated)

Oxalyl chloride (888 µL, 10.2 mmol) is added to a solution of 5-methoxypyrazine-2-carboxylic acid (1.6 g, 10.2 mmol) in ACN (53 mL) and DMF (848 µL). After 15 minutes, the freshly prepared solution is added to a solution of (4aR,7aS)-7a-(5-amino-2-fluoro-phenyl)-6-(5-fluoropyrimidin-2-yl)-4,4a,5,7-tetrahydropyrrolo[3,4-d][1,3]thiazin-2-amine (2.65 g, 7.3 mmol) in a mixture of water (53 mL) and ethanol (53 mL) previously heated at 50° C. The reaction mixture is stirred at 50° C. for one hour, cooled to 22° C., and then stirred overnight at this temperature. The organic solvent is evaporated under vacuum and the aqueous mixture is treated with NaOH 50% w/w aqueous solution to adjust pH=10. A pale cream solid is isolated and washed with additional water. The solid is diluted with isopropyl alcohol (2×) and the solvent is evaporated. The crude material is purified by silica gel chromatography using a gradient of ammoniated methanol (2 N)/DCM. The fractions containing the desired product are combined and solvent is evaporated to give the title compound as an off white solid (1.9 g, 52%). ES/MS (m/z): 499 (M+H).

Alternative Preparation of Crystalline Form 2 N-[3-[(4aR,7aS)-2-Amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide (Hydrated)

ACN (500 mL) is added to DMF (19.2 mL, 248.9 mmol). Oxalyl Chloride (39.3 g, 309.63 mmol) followed by 5-methoxypyrazine-2-carboxylic acid (46.0 g, 298.4 mmol) is added to the DMF/ACN solution. In a separate flask, the aqueous solution of (4aR,7aS)-7a-(5-amino-2-fluoro-phenyl)-6-(5-fluoropyrimidin-2-yl)-4,4a,5,7-tetrahydropyrrolo[3,4-d][1,3]thiazin-2-amine (56.8 g, 156.75 mmol) is added to ACN (500 mL) and the pH is adjusted to 9 with ammonium hydroxide (95 mL). This mixture is then heated to 50–55° C. The oxalyl chloride solution is added dropwise and the mixture is stirred for 3 hours. The pH is adjusted to 8-9 with ammonium hydroxide. The resulting precipitate is filtered, washed with water, and dried to obtain the title compound (123 g). The solid is slurried in acetone (250 mL) for 1.5 hours and filtered. The wet cake is washed with acetone to obtain the title compound (110 g with 90.5% purity by HPLC.). THF (1 L) and activated carbon (9 g) are added to the solid and the mixture is heated to reflux overnight. The mixture is filtered through diatomaceous earth and washed with THF (150 mL). The organic solution is concentrated to 10 volumes and heated to 60° C. Water (430 mL) is added and the mixture is stirred at 60° C. for 8 hours. The mixture is cooled to room temperature and stirred for 10 hours. The resulting solid is filtered, washed with THF/water (7:6) and dried to give the title compound (69 g, 88%) LC-MS: (m/z) 499 (M+H), purity: 98.3%. $^1$H NMR (400 MHz, DMSO-d$_6$) δ ppm 2.99-3.07 (m, 2 H) 3.07-3.14 (m, 1 H) 3.58-3.67 (m, 1 H) 3.68-3.76 (m, 1 H) 3.76-3.84 (m, 1 H) 4.02 (s, 3 H) 4.07 (d, J=10.92 Hz, 1 H) 6.08 (s, 2 H) 7.19 (dd, J=11.98, 8.72 Hz, 1 H) 7.78-7.89 (m, 2 H) 8.41 (s, 1 H) 8.44 (s, 2 H) 8.88 (s, 1 H) 10.60 (s, 1 H).

General Procedure for Preparation of Crystalline Form 2 N-[3-[(4aR,7aS)-2-Amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide (Hydrated)

Slurry N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide in THF at about 23° C. at a concentration of about 71 mg/mL solvent. Heat the slurry with stirring to dissolution which occurs at about 60° C. to about 63° C. Add water to the hot solution to provide a THF:water solvent ratio of about 95:5. Seed crystals of Form 2 N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide are added (about 3 weight % load). The resulting thin slurry is held at about 60° C. to about 63° C. for about 20 minutes, followed by addition of about 5.3 to about 5.5 volumes of water over about 2 to about 4 hours resulting in a THF:water solvent ratio of about 69:31. The slurry is then held at about 60° C. to about 63° C. for about 30 minutes and then cooled to about 23° C. over about 1 hour, and then stirred for about 8-12 hours. The slurry is then filtered, rinsed lightly with THF:water (35:65), and dried for about 8-12 hours under reduced vacuum at about 40° C. to provide the desired crystalline Form 2 N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide which is hydrated.

A prepared sample of crystalline Form 2 N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide is characterized by an XRD pattern using CuKa radiation as having diffraction peaks (2-theta values) as described in Table 1 below. Specifically, the pattern contains a peak at 11.8° in combination with one or more of the peaks selected from the group consisting of 18.6°, 19.3°, and 26.7°; with a tolerance for the diffraction angles of 0.2 degrees.

TABLE 1

X-ray powder diffraction peaks of crystalline Form 2.

| Peak | Angle (2-Theta °) +/-0.2° | Relative Intensity (% of most intense peak) |
|---|---|---|
| 1 | 11.8 | 100.0 |
| 2 | 18.6 | 71.4 |
| 3 | 19.3 | 45.5 |
| 4 | 26.7 | 41.9 |
| 5 | 20.6 | 27.3 |
| 6 | 9.0 | 19.0 |
| 7 | 24.8 | 18.5 |
| 8 | 22.4 | 15.5 |
| 9 | 31.9 | 14.3 |
| 10 | 10.6 | 11.2 |

Crystalline Form 2 N-[3-[(4aR,7aS)-2-Amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide is the stable crystal form at room temperature and relative humidity greater than about 15%.

PREPARATION 48

Crystalline Form 3 N-[3-[(4aR,7aS)-2-Amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide A thermogravimetric analysis pan is loaded with N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide and heated to about 170° C. and held at 170° C. for about 5 minutes. The mixture is cooled to room temperature to provide the title compound.

Alternative Preparation of Crystalline Form 3 N-[3-[(4aR,7aS)-2-Amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide (121 mg) is combined with ACN (5 mL) in a vial, and heated on a 90° C. stir plate. After about 30 minutes, most of the solid dissolves, providing a cloudy solution. Form 3 seeds are added and the sample is stirred for about 1 hour at about 90° C. Heating is removed and the mixture is stirred to provide a bright white solid. The solid is isolated by vacuum filtration, dried under an air stream for about 10 minutes, and then under reduced vacuum at about 80° C. for about 8 to 12 hours to provide the title compound.

A prepared sample of crystalline Form 3 N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide is characterized by an XRD pattern using CuKa radiation as having diffraction peaks (2-theta values) as described in Table 2 below. Specifically, the pattern contains a peak at 15.7° in combination with one or more of the peaks selected from the group consisting of 18.1°, 27.0°, and 19.7°; with a tolerance for the diffraction angles of 0.2 degrees.

TABLE 2

X-ray powder diffraction peaks of crystalline Form 3.

| Peak | Angle (2-Theta °) +/-0.2° | Relative Intensity (% of most intense peak) |
|---|---|---|
| 1 | 15.7 | 100.0 |
| 2 | 18.1 | 98.5 |
| 3 | 27.0 | 80.2 |
| 4 | 19.7 | 75.4 |
| 5 | 25.3 | 75.2 |
| 6 | 18.7 | 50.0 |
| 7 | 17.3 | 49.7 |
| 8 | 5.2 | 44.0 |
| 9 | 10.4 | 41.7 |
| 10 | 11.9 | 37.7 |

EXAMPLE 1

N-[3-[(4aR,7aS)-2-Amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide; toluenesulfonic acid

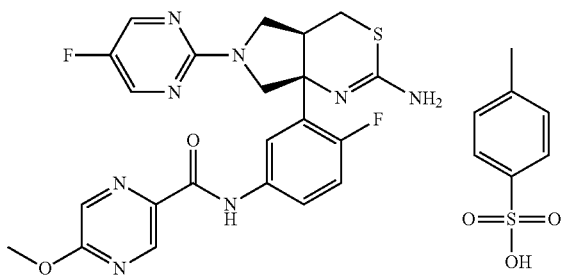 [SMILES: COc1cnc(C(=O)Nc2ccc(F)c([C@]34CN(c5ncc(F)cn5)C[C@H]3CSC(N)=N4)c2)cn1 ; Cc1ccc(S(=O)(=O)O)cc1]

Crystalline Form 2 N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide hydrated (149.15 mg) is added to ethyl acetate (2 mL). The sample is stirred at 1000 rpm at a temperature of 80° C. p-Toluenesulfonic acid (70 mg dissolved in ethyl acetate (1 mL)) is added to the stirring solution, and it is stirred overnight at 80° C. to produce a slurry of a white solid which is isolated by vacuum filtration to provide the title compound.

Alternative Preparation A of N-[3-[(4aR,7aS)-2-Amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide; toluenesulfonic acid N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide (9.5 g, 19 mmol) and p-toluenesulfonic acid (3.80 g, 19.8 mmol) are added to tetrahydrofuran (31 mL), water (7.9 mL), and 2-propanol (8.6 mL). The solution is heated to 40° C. To the warm solution is added 2-propanol (200.0 mL) over approximately 3 hours. The mixture is seeded shortly after the start of the 2-propanol addition with a portion of the title compound (500 mg, 0.75 mmol). After the solvent addition is complete, the mixture is cooled to approximately 20° C. over 1-3 hours. The mixture is heated from approximately 20° C. to approximately 55° C. over a target time of 2 hours. The temperature is held at 55° C. for 1 hour and then cooled to about 20° C. over approximately 4 hours. The slurry is stirred for at least 10 hours at approximately 20° C. The slurry is filtered and the wet cake is washed with water (57 mL). The product is dried in vacuo at 45° C. for at least 10 hours to give the title compound (10.4 g, 81%). ES/MS (m/z): 500 (M+H).

Alternative Preparation B of N-[3-[(4aR,7aS)-2-Amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide; toluenesulfonic acid N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide hydrated (20.7 g) is slurried at 170 rpm in 60:40 THF:H$_2$O (85 mL) in a 500 mL 3-necked round bottomed flask equipped with a nitrogen bubbler, IKA® mechanical motor/agitator attached to a glass shaft having a teflon banana blade, and a thermocouple connected to a programmable J-KEM® temperature controller. p-Toluenesulfonic acid monohydrate (7.6 g, 1.03 eq) is dissolved in a mixture of 60:40 THF:H$_2$O (20 mL) and the solution added all at once to the stirring N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide slurry at 23° C., leading almost immediately to a clear reddish tan solution. The agitation rate is then increased to 200 rpm as over 15 minutes, water (22 mL) is added to the solution, which is then seeded with N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide toluenesulfonic acid (750 mg, 3 wt % seed load) and is then stirred at 23° C. for a further 15 minutes. Over 6 hours, water (226 mL, total solvent of 353 mL; or 13.6 vol., final solvent ratio of 17.5:82.5 THF:H$_2$O) is added to the slurry, which is then stirred overnight (22 hours) at 23° C. The slurry is filtered via vacuum, rinsed with 15:85 THF:H$_2$O (2×20 mL), then left on vacuum for 20 minutes while cracks which form in the product wet cake are manually pressed closed. The wet solids are dried at 40° C. under vacuum for about 72 hours to give the title compound as a white crystalline solid (24.07 g, 90.0 wt %).

The crystalline N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide; toluenesulfonic acid is characterized by an XRD pattern using CuKa radiation as having diffraction peaks (2-theta values) as described in Table 3 below, and in particular having peaks at diffraction angle 2-theta of 5.0° in combination with one or more of the peaks selected from the group consisting of 19.6°, 13.8°, and 18.5°; with a tolerance for the diffraction angles of 0.2 degrees,

TABLE 3

X-ray powder diffraction peaks of crystalline Example 1

| Peak | Angle (2-Theta°) +/-0.2° | Relative Intensity (% of most intense peak) |
|---|---|---|
| 1 | 5.0 | 100.0 |
| 2 | 13.4 | 22.9 |
| 3 | 13.8 | 37.3 |

TABLE 3-continued

X-ray powder diffraction peaks of crystalline Example 1

| Peak | Angle (2-Theta°) +/−0.2° | Relative Intensity (% of most intense peak) |
|---|---|---|
| 4 | 14.4 | 20.2 |
| 5 | 15.3 | 28.8 |
| 6 | 17.5 | 25.9 |
| 7 | 18.5 | 30.7 |
| 8 | 19.6 | 45.8 |
| 9 | 20.4 | 17.7 |
| 10 | 25.6 | 30.1 |

It has been found that below about 15% relative humidity, crystalline form 1 of the free base of N-{3-[(4aR,7aS)-2-amino-6-(5-fluoropyrimidin-2-yl)-4a,5,6,7-tetrahydropyrrolo[3,4-d][1,3]thiazin-7a(4H)-yl]-4-fluoro-phenyl}-5-methoxypyrazine-2-carboxamide is present, while above about 15% relative humidity, crystalline form 2 of N-{3-[(4aR,7aS)-2-amino-6-(5-fluoropyrimidin-2-yl)-4a,5,6,7-tetrahydropyrrolo[3,4-d][1,3]thiazin-7a(4H)-yl]-4-fluoro-phenyl}-5-methoxypyrazine-2-carboxamide predominates. Such physical instability is undesirable, particularly for a pharmaceutical drug substance or drug product, both of which are subject to regulatory controls regarding the solid state forms. In contrast to the crystalline forms of the free base, the tosylate salt possesses improved physical stability over a wide range of relative humidities (5-95%). As such, the tosylate salt of N-{3-[(4aR,7aS)-2-amino-6-(5-fluoropyrimidin-2-yl)-4a,5,6,7-tetrahydropyrrolo[3,4-d][1,3]thiazin-7a(4H)-yl]-4-fluoro-phenyl}-5-methoxypyrazine-2-carboxamide essentially avoids the humidity dependent phase transformations associated with the corresponding crystalline free base forms. Furthermore, the tosylate salt of N-{3-[(4aR,7aS)-2-amino-6-(5-fluoropyrimidin-2-yl)-4a,5,6,7-tetrahydropyrrolo[3,4-d][1,3]thiazin-7a(4H)-yl]-4-fluoro-phenyl}-5-methoxypyrazine-2-carboxamide was found to have a substantially lower amount of solvent retained in the crystal of about 1.3% compared to about 7.7% solvent retained for the HCl salt of N-{3-[(4aR,7aS)-2-amino-6-(5-fluoropyrimidin-2-yl)-4a,5,6,7-tetrahydropyrrolo[3,4-d][1,3]thiazin-7a(4H)-yl]-4-fluoro-phenyl}-5-methoxypyrazine-2-carboxamide. The increased likelihood of the free base to undergo phase transitions during long term storage can lead to variability in properties, such as solubility or dissolution rate, which may compromise the performance of the drug product. It also poses the additional risk of collapse of the crystal structure(s) to an amorphous form or accumulation of defects and disorder, which could lead to chemical instability and reduced shelf-life of the drug product.

In Vitro Assay Procedures:

For in vitro enzymatic and cellular assays, test compounds are prepared in DMSO to make up a 10 mM stock solution. The stock solution is serially diluted in DMSO to obtain a ten-point dilution curve with final compound concentrations ranging from 10 mM to 0.05 nM in a 96-well round-bottom plate before conducting the in vitro enzymatic and whole cell assays.

In Vitro Protease Inhibition Assays:

Expression of Human BACE1

Human BACE1 (accession number: AF190725) is cloned from total brain cDNA by RT-PCR. The nucleotide sequences corresponding to amino acid sequences #1 to 460 are inserted into the cDNA encoding human $IgG_1$ (Fc) polypeptide (Vasser, et al., *Science,* 286, 735-741 (1999)). This fusion protein of BACE1(1-460) and human Fc, named huBACE1:Fc, is constructed into the pJB02 vector. Human BACE1(1-460):Fc (huBACE1:Fc) is transiently expressed in HEK293 cells. 250 µg cDNA of each construct is mixed with Fugene 6 and added to 1 liter HEK293 cells. Four days after the transfection, conditioned media are harvested for purification.

Purification of huBACE1:Fc huBACE1:Fc is purified by Protein A chromatography. The enzyme is stored at −80° C. in small aliquots.

BACE1 FRET Assay

Serial dilutions of test compounds are prepared as described above. Compounds are further diluted 20× in $KH_2PO_4$ buffer. Ten µL of each dilution is added to each well on row A to H of a corresponding low protein binding black plate containing the reaction mixture (25 µL of 50 mM $KH_2PO_4$, pH 4.6, 1 mM TRITON® X-100, 1 mg/mL Bovine Serum Albumin, and 15 µM of FRET substrate) (See Yang, et. al., *J. Neurochemistry,* 91(6) 1249-59 (2004)). The content is mixed well on a plate shaker for 10 minutes. Fifteen µL of two hundred µM human BACE1(1-460):Fc (See Vasser, et al., *Science,* 286, 735-741 (1999)) in the $KH_2PO_4$ buffer is added to the plate containing substrate and test compounds to initiate the reaction. The RFU of the mixture at time 0 is recorded at excitation wavelength 355 nm and emission wavelength 460 nm, after brief mixing on a plate shaker. The reaction plate is covered with aluminum foil and kept in a dark humidified oven at room temperature for 16 to 24 h. The RFU at the end of incubation is recorded with the same excitation and emission settings used at time 0. The difference of the RFU at time 0 and the end of incubation is representative of the activity of BACE1 under the compound treatment. RFU differences are plotted versus inhibitor concentration and a curve is fitted with a four-parameter logistic equation to obtain the $EC_{50}$ and $IC_{50}$ values. (See Sinha, et al., *Nature,* 402, 537-540 (2000)).

The compound of Preparation 46 is tested essentially as described above and exhibited a BACE1 $IC_{50}$ of 0.615 nM (±0.101, n=5) [Mean±SEM; SEM=standard error of the mean]. This data demonstrates that the compound of Preparation 46 inhibits purified recombinant BACE1 enzyme activity in vitro.

PDAPP Primary Neuronal Assay

A confirmatory whole cell assay is also run in primary neuronal cultures generated from PDAPP transgenic embryonic mice. Primary cortical neurons are prepared from Embryonic Day 16 PDAPP embryos and cultured in 96 well plates ($15 \times 10^4$ cells/well in DMEM/F12 (1:1) plus 10% FBS). After 2 days in vitro, culture media is replaced with serum free DMEM/F12 (1:1) containing B27 supplement and 2 µM (final) of Ara-C (Sigma, C1768). At day 5 in vitro, neurons are incubated at 37° C. for 24 hours in the presence/absence of inhibitors (diluted in DMSO) at the desired concentration. At the end of the incubation, conditioned media are analyzed for evidence of beta-secretase activity, for example, by analysis of Abeta peptides. Total Abeta peptides (Abeta 1-x) are measured by a sandwich ELISA, using monoclonal 266 as a capture antibody and biotinylated 3D6 as reporting antibody. Alternatively, Abeta 1-40 and Abeta 1-42 peptides are measured by a sandwich ELISA, using monoclonal 2G3 as a capture antibody for Abeta 1-40, and monoclonal 21F12 as a capture antibody for Abeta 1-42. Both Abeta 1-40 and Abeta 1-42 ELISAs use biotinylated 3D6 as the reporting antibody. The concentration of Abeta released in the conditioned media following the compound treatment corresponds to the activity of BACE1 under such conditions. The 10-point inhibition curve is plotted and fitted with the four-parameter logistic equation to obtain the $EC_{50}$ and $IC_{50}$ values for the Abeta-lowering effect. The compound of Preparation 46 is tested essentially as described above and exhibited the following activity for Abeta lowering effect:

TABLE 4

| Preparation | PDAPP Neuron A-beta (1-40) ELISA $IC_{50}$ (nM) | PDAPP Neuron A-beta (1-42) ELISA $IC_{50}$ (nM) |
| --- | --- | --- |
| 46 | 0.275 (±0.176, n = 4) | 0.228 (±0.244, n = 3) |

Mean ± SEM; SEM = standard error of the mean

These data demonstrate that the compound of Preparation 46 inhibits Abeta production in whole cells.

In Vivo Inhibition of Beta-Secretase

Several animal models, including mouse, guinea pig, dog, and monkey, may be used to screen for inhibition of beta-secretase activity in vivo following compound treatment. Animals used in this invention can be wild type, transgenic, or gene knockout animals. For example, the PDAPP mouse model, prepared as described in Games et al., *Nature* 373, 523-527 (1995), and other non-transgenic or gene knockout animals are useful to analyze in vivo inhibition of Abeta and sAPPbeta production in the presence of inhibitory compounds. Generally, 2 to 12 month old PDAPP mice, gene knockout mice or non-transgenic animals are administered compound formulated in vehicles, such as corn oil, cyclodextran, phosphate buffers, PHARMASOLVE®, or other suitable vehicles. One to twenty-four hours following the administration of compound, animals are sacrificed, and brains as well as cerebrospinal fluid and plasma are removed for analysis of Abetas, C99, and sAPP fragments. (See May, et al., *Journal of Neuroscience*, 31, 16507-16516 (2011)).

For standard in vivo pharmacology studies, animals are dosed with various concentrations of compound and compared to a vehicle-treated control group dosed at the same time. For some time course studies, brain tissue, plasma, or cerebrospinal fluid is obtained from selected animals, beginning at time 0 to establish a baseline. Compound or appropriate vehicle is administered to other groups and sacrificed at various times after dosing. Brain tissue, plasma, or cerebrospinal fluid is obtained from selected animals and analyzed for the presence of APP cleavage products, including Abeta peptides, sAPPbeta, and other APP fragments, for example, by specific sandwich ELISA assays. At the end of the test period, animals are sacrificed and brain tissues, plasma, or cerebrospinal fluid are analyzed for the presence of Abeta peptides, C99, and sAPPbeta, as appropriate. Brain tissues of APP transgenic animals may also be analyzed for the amount of beta-amyloid plaques following compound treatment. "Abeta 1-x peptide" as used herein refers to the sum of Abeta species that begin with residue 1 and ending with a C-terminus greater than residue 28. This detects the majority of Abeta species and is often called "total Abeta".

Animals (PDAPP or other APP transgenic or non-transgenic mice) administered an inhibitory compound may demonstrate the reduction of Abeta or sAPPbeta in brain tissues, plasma or cerebrospinal fluids and decrease of beta amyloid plaques in brain tissue, as compared with vehicle-treated controls or time zero controls. For Preparation 46, three hours after administration of 0.3, 1, or 3 mg/kg oral dose of the compound, Abeta 1-x peptide levels are reduced approximately 31%, 39%, and 61% in brain hippocampus, and approximately 28%, 42%, and 64% in brain cortex, respectively compared to vehicle-treated mice.

Given the activity of Preparation 46 against BACE enzyme in vitro, these Abeta lowering effects are consistent with BACE inhibition in vivo, and further demonstrate CNS penetration of N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide.

We claim:

1. A compound which is a tosylate salt of N-[3-[(4aR,7aS)-2-amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide which is crystalline.

2. The tosylate salt according to claim 1 which is characterized by a substantial peak in the X-ray diffraction spectrum, at diffraction angle 2-theta of 5.0° in combination with one or more of the peaks selected from the group consisting of 19.6°, 13.8°, and 18.5°; with a tolerance for the diffraction angles of 0.2 degrees.

3. A method of treating Alzheimer's disease in a patient, comprising administering to a patient in need of such treatment an effective amount of a compound according to claim 1.

4. A method of treating the progression of mild cognitive impairment to Alzheimer's disease in a patient, comprising administering to a patient in need of such treatment an effective amount of a compound according to claim 1.

5. A pharmaceutical composition, comprising a compound according to claim 1 with one or more pharmaceutically acceptable carriers, diluents, or excipients.

* * * * *